(12) United States Patent
Bishop et al.

(10) Patent No.: US 11,559,811 B2
(45) Date of Patent: Jan. 24, 2023

(54) CELL CULTURE SYSTEM AND METHOD

(71) Applicant: Lonza Ltd., Visp (CH)

(72) Inventors: Jason Bishop, Walkersville, MD (US); Steven Roberts, Potomac, MD (US)

(73) Assignee: Lonza Ltd., Visp (CH)

( * ) Notice: Subject to any disclaimer, the term of this patent is extended or adjusted under 35 U.S.C. 154(b) by 823 days.

(21) Appl. No.: 15/891,432

(22) Filed: Feb. 8, 2018

(65) Prior Publication Data
US 2018/0229241 A1    Aug. 16, 2018

Related U.S. Application Data

(60) Provisional application No. 62/457,341, filed on Feb. 10, 2017.

(51) Int. Cl.
| | | |
|---|---|---|
| *B01L 3/00* | (2006.01) | |
| *C12M 1/00* | (2006.01) | |
| *C12M 1/34* | (2006.01) | |

(52) U.S. Cl.
CPC .......... *B01L 3/561* (2013.01); *B01L 3/52* (2013.01); *C12M 23/58* (2013.01); *C12M 27/18* (2013.01); *C12M 29/00* (2013.01); *C12M 29/26* (2013.01); *C12M 41/00* (2013.01); *C12M 47/02* (2013.01); *B01L 2300/123* (2013.01); *B01L 2400/086* (2013.01)

(58) Field of Classification Search
CPC ...... B01L 3/561; B01L 3/52; B01L 2300/123; B01L 2400/086; C12M 23/58; C12M 27/18; C12M 29/00; C12M 29/26; C12M 41/00; C12M 47/02
See application file for complete search history.

(56) References Cited

U.S. PATENT DOCUMENTS

| | | | |
|---|---|---|---|
| 5,656,491 A | 8/1997 | Cassani et al. | |
| 6,234,538 B1 * | 5/2001 | Lauer | A61M 39/14 285/3 |

(Continued)

FOREIGN PATENT DOCUMENTS

| | | |
|---|---|---|
| CN | 1694950 | 11/2005 |
| CN | 101559246 | 10/2009 |

(Continued)

OTHER PUBLICATIONS

Terumo BCT, "Human Discovery Machine Reliability" tubing welder brochure, p. 2, 4 (Year: 2019).*

(Continued)

*Primary Examiner* — William H. Beisner
*Assistant Examiner* — Danielle B Henkel
(74) *Attorney, Agent, or Firm* — Dority & Manning, P.A.

(57) ABSTRACT

A bioprocess system and a method for incubating, growing and harvesting cell cultures is described. Also disclosed is a bioprocess container that can be used with the system. In one aspect of the present disclosure, the bioprocess system includes bioprocess tubes and cell culture tubes having particular dimensions and being made from specific materials that allow the tubes to be welded together while preventing open connections and/or ruptures. In this manner, bioprocess containers can be connected and disconnected from a cell culture apparatus without having to perform the manipulation within a closed environment and without associated monitoring.

17 Claims, 11 Drawing Sheets

(56) References Cited

U.S. PATENT DOCUMENTS

| | | |
|---|---|---|
| 7,629,167 B2 | 12/2009 | Hodge et al. |
| 7,897,379 B2 | 3/2011 | Kenney et al. |
| 8,163,555 B2 | 4/2012 | Antwiler |
| 8,177,082 B2 | 5/2012 | Cattadoris et al. |
| 8,178,345 B2 | 5/2012 | Bennett et al. |
| 8,216,828 B2 | 7/2012 | Cattadoris et al. |
| 8,298,054 B2 | 10/2012 | Hodge et al. |
| 9,045,721 B2 | 6/2015 | Martin et al. |
| 9,284,523 B2 | 3/2016 | Dodd et al. |
| 9,388,373 B2 | 7/2016 | Rao et al. |
| 10,676,705 B2 | 6/2020 | Henon et al. |
| 2003/0028156 A1* | 2/2003 | Juliar ................. A61M 1/0231 604/310 |
| 2003/0157709 A1* | 8/2003 | DiMilla ................ C12M 29/10 435/325 |
| 2008/0118974 A1 | 5/2008 | Martin et al. |
| 2009/0305626 A1 | 12/2009 | Hope |
| 2010/0105138 A1* | 4/2010 | Dodd .................... C12M 29/00 435/383 |
| 2010/0216229 A1 | 8/2010 | Kenney et al. |
| 2011/0220290 A1* | 9/2011 | Hlavinka ............ B29C 66/7373 156/380.1 |
| 2011/0280797 A1 | 11/2011 | Mohtadi et al. |
| 2012/0077429 A1 | 3/2012 | Wernimont et al. |
| 2015/0037882 A1 | 2/2015 | Rowley et al. |
| 2018/0104147 A1 | 4/2018 | Ware et al. |

FOREIGN PATENT DOCUMENTS

| | | |
|---|---|---|
| JP | 2004129568 | 4/2004 |
| WO | WO 86/01531 | 3/1986 |
| WO | WO 2015/148390 | 1/2015 |

OTHER PUBLICATIONS

Terumo BCT, SCD (R) IIB Sterile Tubing Welder, p. 4 (Year: 2014).*

PCT/US2018/017321, International Search Report and Written Opinion dated May 30, 2018.

* cited by examiner

CELL CULTURE SYSTEM AND METHOD

RELATED APPLICATIONS

The present application is based on and claims priority to U.S. Provisional Patent application Ser. No. 62/457,341, filed on Feb. 10, 2017, which is incorporated herein by reference.

BACKGROUND

New processes and procedures are developing in the rapidly changing field of biotechnology that require packaging of sterile liquid media and reagents in bulk, flexible, disposable container systems. Bioprocess containers are generally designed as single use containers for packaging of cell culture media including reagents and buffers, as well as containment and storage vessels for final products yielded from downstream manufacturing processes.

Closed system processes for inoculation of cell culture vessels generally involve transfer of a cell suspension into a bioprocess container having a larger media volume. The bioprocess container is then attached to a culture vessel and the diluted cell suspension contained in the bioprocess container is transferred into the culture vessel. Once inoculated into the culture vessel, the cell suspension is exposed to conditions that cause cell growth and reproduction to occur resulting in a growing cell culture. During growth of the cell culture, depending upon the type of cells being grown, the cell culture media surrounding the cells may need to be replaced or replenished. After the cell culture has grown to a desired extent, it is then necessary to harvest the cells from the cell culture apparatus. Each of these procedures requires connecting and disconnecting various different bioprocess containers from the cell culture apparatus.

Currently, the most common methodology to disconnect and connect bioprocess containers to cell culture apparatus during the growth of a cell culture is to use medical plastic circular connectors (MPC connectors). MPC connectors allow for easy attachment and detachment of bioprocess containers. MPC connectors, however, form an open connection during the attachment or detachment process. As used herein, an open connection refers to a tube that is open to the ambient environment even if for a short amount of time. Thus, the use of MPC connectors adds significant complexity to the process by which cell cultures are grown. For instance, because open connections occur with the use of MPC connectors, the connections must be made in a strictly controlled closed environment with highly filtered air and must also require extensive environmental monitoring. In addition, the use of MPC connectors requires manual manipulation within the highly controlled environment, making what should be a simple procedure for connecting or disconnecting a tube prone to operator variability and error. The use of MPC connectors creates a risk of contamination at every stage of the process, as well as requiring significant amounts of operator time and manipulating the vessels. Due to the necessity of the environmentally controlled area, the use of MPC connectors also requires lab engineering as well as significant laboratory space while also requiring additional time not only to move and manipulate the vessels within a controlled environment but also to analyze environmental data to ensure that no contamination has occurred.

In the past, those skilled in the art have suggested to weld tubes together instead of using MPC connectors. Unfortunately, welding has met with variability and inconsistent results. In particular, significant amounts of welding errors have been experienced. A welding error can lead to an open connection, which can compromise the entire cell culture being grown in addition to creating the risk of environmental contamination.

In view of the above, a need exists for a system and method for attaching and disconnecting bioprocess containers to a cell culture apparatus. For example, a need exists for a method and system for connecting and disconnecting bioprocess containers to and from a cell culture apparatus without creating an open connection and without having to operate the procedure within a controlled environment. A need also exists for an improved bioprocess container that can be easily connected and disconnected from a cell culture apparatus without experiencing any problems related to flow control.

SUMMARY

The present disclosure is generally directed to a system and method for growing cell cultures and to a bioprocess container for facilitating the addition or removal of a cell culture media to and from a cell culture apparatus. In one embodiment, the present disclosure is directed to a method by which a multilayer cell culture apparatus can be seeded (or inoculated), fed, harvested, manipulated, and connected using a fully closed and aseptic system for cell expansion. The method and system allows for cells and reagents to be added and removed from the cell culture apparatus without the risk of open connections, allowing the culture process to occur safely with reduced environmental controls compared to other methods used in the past. The method and system of the present disclosure increases safety, is more scalable, and reduces the number of manual manipulations required to work with a cell culture apparatus for growing a cell culture.

In one embodiment, the present disclosure is directed to a method for delivering materials and removing materials from a cell culture apparatus. The method includes blocking the flow of fluids through an end portion of at least one bioprocess tube, the bioprocess tube is in fluid communication with a cell culture apparatus. The cell culture apparatus comprises a plurality of cell culture chambers in a stacked arrangement. In one embodiment, the cell culture apparatus is designed to grow cell cultures in an air or gas free environment in which each chamber is separated from another chamber by a selectively permeable membrane that allows certain constituents from a cell culture media to move from one chamber to another. The bioprocess tube connected to the cell culture apparatus can be made from a thermoplastic elastomer, such as a silicone and can be configured to deliver and remove materials from the cell culture apparatus.

The method of the present disclosure further comprises blocking the flow of fluids through an end portion of a cell culture linking tube that is in communication with a bioprocess container. The bioprocess container can contain a cell culture media. As used herein, a cell culture media can comprise any composition containing cells, a reagent, a nutrient composition for cells, a proteolytic agent, a quench composition, or the like. In accordance with the present disclosure, the end portion of the bioprocess tube is cut and welded to the end portion of the cell culture linking tube without creating an open connection. For instance, the end portions of the bioprocess tube and the cell culture linking tube can be simultaneously cut and welded together in a manner so that no open connection is formed. In accordance with the present disclosure, the bioprocess tube and the cell culture linking tube have a cell wall thickness of at least 2.25 mm (0.09 in), such as at least 2.75 mm (0.1 in), such as at least 3 mm (0.11 in). The inside diameter of the bioprocess tube and the cell culture linking tube can generally be from about 7.5 mm (0.3 in) to about 12.5 mm (0.5 in), such as from about 8.5 mm (0.35 in) to about 10.5 mm (0.4 in).

Once the bioprocess tube and the cell culture linking tube have been welded together, fluid flow through the bioprocess tube and the cell culture linking tube are unblocked. The cell culture media in the bioprocess container is then feed through the linking tube and bioprocess tube to the cell culture apparatus.

In one embodiment, the method of the present disclosure further comprises the steps of blocking fluid flow through the end portion of the cell culture linking tube, blocking fluid flow through the bioprocess tube, and blocking fluid flow through an end portion of a second cell culture linking tube in communication with a second bioprocess container. The second bioprocess container, for instance, may contain a cell culture media. In accordance with the present disclosure, the bioprocess tube and the end portion of the second cell culture linking tube are cut and welded together in a manner that does not produce an open connection. Fluid flow through the bioprocess tube and through the second cell culture linking tube are then unblocked allowing the cell culture media in the second bioprocess container to feed through the second cell culture linking tube and bioprocess tube and into the cell culture apparatus. Through the processes described above, two different cell culture medias are feed to the cell culture apparatus from different bioprocess containers without creating an open connection in the system.

In one embodiment, for instance, the cell culture media in the first bioprocess container comprises viable cells for inoculation into the cell culture apparatus. The cell culture media contained in the second bioprocess container, on the other hand, may comprise a nutrient composition for promoting growth of the cell culture in the cell culture apparatus.

In one embodiment, in order to harvest cells from the cell culture apparatus, the second bioprocess container may contain a proteolytic agent that is fed to the cell culture apparatus for causing the individual cells to detach from the walls of the cell culture apparatus. Once detached, the harvested cells can be fed back into the second bioprocess container.

In one particular embodiment, the second cell culture linking tube includes a Y connector that connects to a first Y tube and a second Y tube. The first Y tube may connect to the second bioprocess container, while the second Y tube may connect to a third bioprocess container. The second bioprocess container may contain a proteolytic agent, while the third bioprocess container may contain a quenching composition. In this embodiment, when it is time to harvest cells from a cell culture apparatus, the proteolytic agent is first fed to a cell culture apparatus from the second bioprocess container. Next, the quenching composition is fed to the cell culture apparatus from the third bioprocess container. In order to harvest the cells from the cell culture apparatus, the cells are drained from the cell culture apparatus into either the second bioprocess container or the third bioprocess container. In one embodiment, the harvested cells are fed to the second bioprocess container and a quick disconnect is used to separate the second bioprocess container from the first Y tube.

The present disclosure is also directed to a bioprocess system. The bioprocess system includes a cell culture apparatus for growing and harvesting cell cultures. The cell culture apparatus comprises a plurality of cell culture chambers in a stacked arrangement. The cell culture apparatus includes at least one bioprocess tube comprised of a thermoplastic elastomer that has a diameter and a wall thickness. The system further includes a plurality of bioprocess containers. The containers define a hollow enclosure for holding a cell culture media. Each container includes a cell culture linking tube in communication with the hollow enclosure. The linking tube has a diameter, a wall thickness and is made from a material that are all compatible with the diameter, the wall thickness and the thermoplastic elastomer of the bioprocess tube.

In accordance with the present disclosure, the cell culture linking tube of each bioprocess container is configured to be welded to the bioprocess tube of the cell culture apparatus so that each bioprocess container can be selectively placed in fluid communication with the cell culture apparatus. In order to ensure that a sterile and aseptic connection is made between the cell culture linking tube and the bioprocess tube, both the cell culture linking tube and the bioprocessed tube have a wall thickness of at least 2.25 mm (0.09 in), such as at least 2.75 mm (0.1 in), such as at least 3 mm (0.11 in). The wall thickness of the cell culture linking tube and the bioprocess tube, for instance, can be from about 2.75 mm (0.1 in) to about 3.75 mm (0.15 in). In addition to having a wall thickness as described above, the inside diameter of the bioprocess tube and the cell culture linking tube can be from about 6.25 mm (0.25 in) to about 12.5 mm (0.5 in), such as from about 7.5 mm (0.3 in) to about 11.5 mm (0.45 in).

The dimensions of the cell culture linking tube and the bioprocess tube ensure that a leak proof connection is made between the tubes during the welding process. In one embodiment, for instance, when one of the cell culture linking tubes is connected to the bioprocess tube of the cell culture apparatus, a weld structure is formed during the welding process. The weld structure includes a leak proof flange encircling the location where the cell culture linking tube has been attached to the bioprocess tube. The flange, for instance, can have a height of greater than about 0.2 mm, such as greater than about 0.3 mm, such as greater than about 0.4 mm.

In one embodiment, the system further includes a biowelding apparatus that is configured to simultaneously cut and weld together the bioprocess tube with one of the cell culture linking tubes for placing the cell culture apparatus in fluid communication with one of the bioprocess containers for feeding materials or removing material from the cell culture apparatus without creating an open connection in the bioprocess tube. The system can further comprise flow stop devices for preventing the flow of fluid within the bioprocess tube and the linking tubes during cutting and welding of the tubes in the biowelding apparatus.

In one embodiment, the bioprocess tube in each of the cell culture linking tubes have the same diameter, wall thickness and are made from the same thermoplastic elastomer. The thermoplastic elastomer, for instance, may comprise a silicone polymer, a polyvinyl chloride polymer, a polypropylene polymer, a polyethylene polymer, or a polyester polymer.

The bioprocess system can include a single bioprocess container or can contain a plurality of bioprocess containers. In one embodiment, for instance, the system includes at least three bioprocess containers. For example, one of the containers can contain a reagent or a cell nutrient composition. Another container can remain empty for receiving a liquid media from a cell culture apparatus. Another bioprocess container, on the other hand, may contain a composition designed to assist in harvesting cells from the cell culture apparatus. For example, the bioprocess container may contain a proteolytic agent, such as an enzyme. Each of the bioprocess containers can have a volume designed for the particular application and purpose. For example, the containers can have a volume from about 0.5 liters to about 25 liters.

The present disclosure is also directed to a bioprocess container that is designed to be used with a cell culture apparatus. The bioprocess container comprises a flexible container having a first end and a second and opposite end. The flexible container defines an interior volume for holding a fluid, such as a cell culture media. The flexible container includes a plurality of ports located at the first end of the container. Each port is in fluid communication with the interior volume. One of the ports is connected to a cell culture linking tube. The linking tube, for instance, may have a wall thickness of at least about 2.25 mm, such as at least about 3 mm and can have an inside diameter of from about 8.5 mm to about 10.5 mm.

In accordance with the present disclosure, the bioprocess container can further include a flow guiding device positioned at the first end of the flexible container in communication with each of the ports. The flow guiding device can comprise a single-piece structure made from a rigid material, such as a rigid polymer. The flow guiding device defines a plurality of spaced apart passageways corresponding to the plurality of ports. Each of the passageways on the flow guiding device can have a diameter of from about 6.25 mm (0.25 in) to about 12.5 mm (0.5 in), such as from about 7.5 mm (0.3 in) to about 11.5 mm (0.45 in).

The present disclosure is also directed to the ornamental design of a bioprocess container as shown in the figures.

Other objects and advantages of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which.

DETAILED DESCRIPTION

Figure 1:
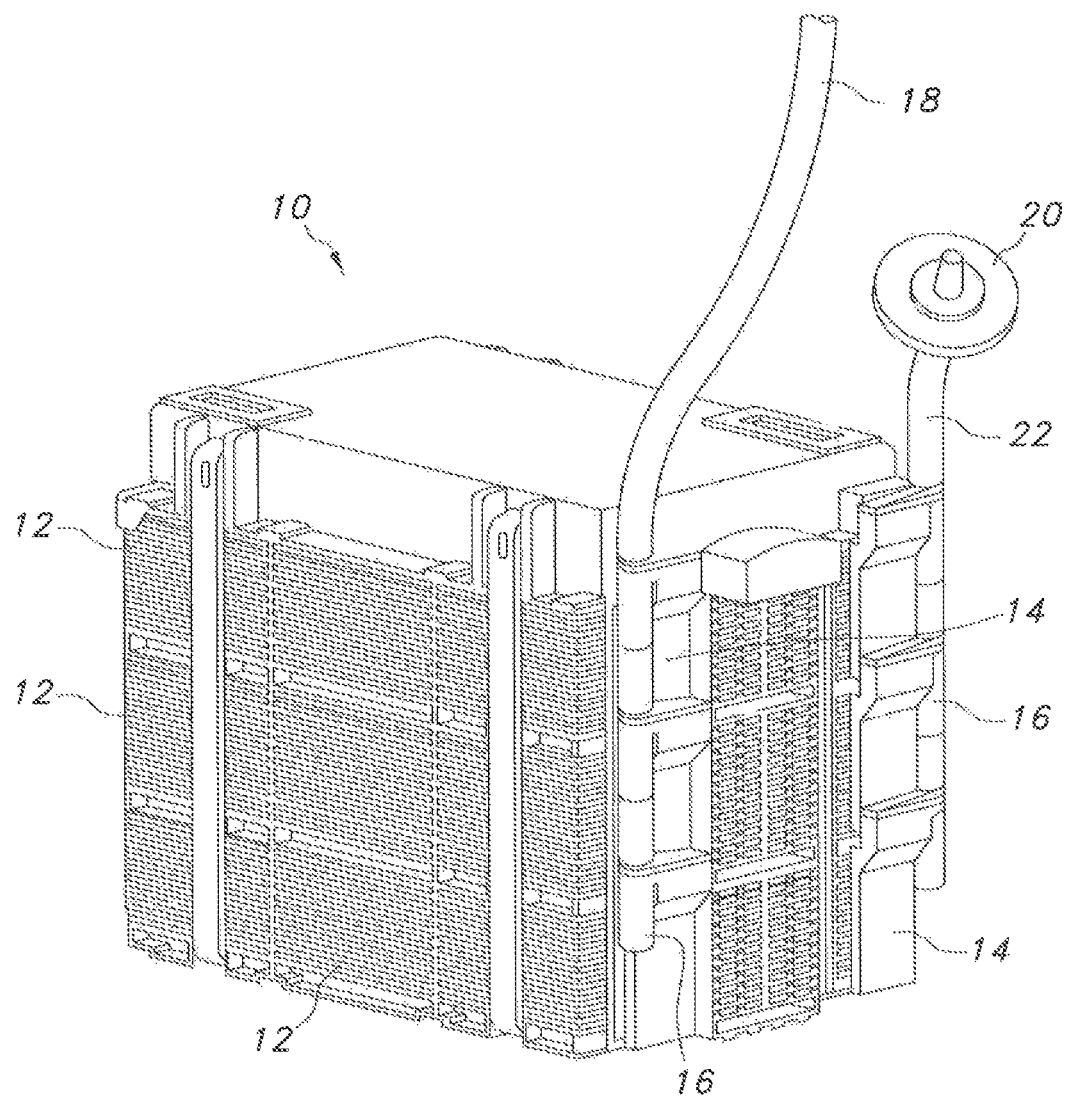
FIG. 1 is perspective view of one embodiment of a cell culture apparatus that may be used with the system of the present disclosure.

It is to be understood by one of ordinary skill in the art that the present discussion is a description of exemplary embodiments only, and is not intended as limiting the broader aspects of the present disclosure.

In general, the present disclosure is directed to a system and method for growing cell cultures. More particularly, the present disclosure is directed to a method for feeding materials to and removing materials from a cell culture apparatus in order to inoculate a cell culture within the apparatus, grow the cell culture, and/or harvest the cell culture. The cell culture can be grown for numerous reasons. For example, in one embodiment, the cell culture can be grown for cell therapy. Cell therapy is the prevention, treatment, cure or mitigation of disease or injuries in humans by the administration of autologous, allogeneic or xenogeneic cells that have been manipulated or altered ex vio. One goal of cell therapy is to repair, replace or restore damaged tissues or organs.

In addition to cell therapy, however, cell cultures can be grown in accordance with the present disclosure for numerous other reasons. The cell cultures, for instance, may be used for research or for various other applications.

Currently, a major obstacle to the production of biopharmaceuticals is the cost associated with maintenance, sterilization and validation of cell culture devices and bioprocess containers used with the devices. When growing cell cultures, for instance, the maintenance of sterility is always a critical concern. The final product, for instance, cannot be sterilized by traditional means, such as by using sterile filtration, heat, radiation or chemical means. All of the above methods, for instance, would destroy or otherwise damage the living cells being produced. To ensure the sterility of the final product, processes for producing cell cultures must always remain tightly controlled with regard to sterility. At the same time, different cell culture media, such as liquid reagents, the cells themselves, or proteolytic compositions, must be moved in and out of the cell culture vessels. Typically, these transfers are performed in a manner that opens up the system to an external environment, thereby increasing the risk of foreign contaminants entering the system.

In accordance with the present disclosure, however, a method and system has been developed in which cell culture media can be moved into and out of a cell culture apparatus without producing an open connection. For instance, by creating a system of bioprocess containers, tubing, and relatively simple manipulations, open connections within the system of the present disclosure can be eliminated.

In general, the system of the present disclosure involves the use of particularly designed bioprocess containers and/or the use of particularly designed biotubing in conjunction with a multilayer cell culture apparatus. The biotubes used in accordance with the present disclosure, for instance, generally have a relatively large inside diameter in conjunction with an expanded wall thickness in addition to being made from an elastomeric polymer. The dimensions of the biotube allow for connections to be made between bioprocess containers and the cell culture apparatus using a sterile welder and without forming an open connection. In addition, the dimensions of the biotubes have also been found to reduce kinking of the line when clamped, during incubation, and during manipulation. This reduced tendency to form kinks and potentially block air flow has the benefit of reducing manipulations and subsequent operator error. Through the use of the materials of the present disclosure, the entire system can remain a closed system which greatly reduces the risk of anything external entering the cell culture apparatus and contaminating the cell culture being grown. Additionally, by utilizing welding, sterile aseptic connections and sterile aseptic disconnections can be executed in an environment with reduced engineering and personnel controls. Consequently, in accordance with the present disclosure, a bioprocess tube can be disconnected and a new tube can be connected to a cell culture apparatus without having to operate within a controlled environment, such as a ventilated enclosure or fume hood.

Referring to FIG. 1, for instance, one embodiment of a cell culture apparatus 10 that may be used in accordance with the present disclosure is shown. The cell culture apparatus 10 in FIG. 1 is multilayered having layers of cell culture chambers connected via manifolds that allow the layers of cell culture chambers to be filled, in series or in parallel, with a fluid, such as a cell culture media.

For instance, referring to FIG. 1, the cell culture apparatus 10 includes a plurality of cell culture chambers 12. In the embodiment illustrated, the apparatus includes three separate sub units that have been stacked together. The cell culture apparatus 10 can include generally greater than 10 cell culture chambers, such as greater than about 15 cell culture chambers, such as greater than about 20 cell culture chambers, such as greater than about 25 cell culture chambers, such as greater than about 30 cell culture chambers, such as greater than about 35 cell culture chambers, such as greater than about 40 cell culture chambers, such as greater than about 45 cell culture chambers, such as even greater than about 50 cell culture chambers in a stacked arrangement. In general, the cell culture apparatus 10 contains less than about 200 separate chambers, such as less than about 100 separate chambers. In the embodiment illustrated in FIG. 1, for instance, the cell culture apparatus 10 includes 36 cell culture chambers.

The cell culture apparatus 10 includes a plurality of manifolds 14 that are in communication with fluid channels 16. The cell culture apparatus 10 further includes a bioprocess tube 18 and a filter 20 connected to a filter tube 22. In order to fill the cell culture apparatus 10 with a cell culture media, the cell culture media can be fed through the bioprocess tube 18 and into the fluid channel 16. The fluid channel 16 is in communication with the manifolds 14 which direct the cell culture media into the individual cell culture chambers 12. As the cell culture apparatus 10 is filled with a cell culture media, gases, such as air, are displaced within the apparatus and exit through the filter tube 22 and the gas filter 20.

In one embodiment, the cell culture apparatus may include a plurality of sub-units or cell culture vessels. Each cell culture vessel may include a plurality of cell culture chambers. The cell culture vessels can be connected in series or in parallel using an external manifold.

The cell culture apparatus 10 can be made from any suitable materials. In one embodiment, the cell culture apparatus is designed such that the cell culture chambers become completely filled with the cell culture media and that all gases contained within the cell culture apparatus are expelled through the filter 20. If the cell culture apparatus 10 is designed to comprise only a liquid system, the apparatus can include gas permeable portions that allow gas exchange between a cell culture chamber and the ambient of the cell culture apparatus. For example, in one embodiment, each cell culture chamber can include a gas permeable section formed by a gas permeable film. The gas permeable film can form at least a portion of the cell culture chamber and allow gas to transfer between the chamber and the ambient environment. The gas permeable film, however, can also be designed to be liquid impermeable. In one embodiment, for instance, the cell culture apparatus 10 can include gas spaces within the apparatus that are positioned adjacent to the gas permeable film. The spaces allow the film to exchange gases with the outside environment. For example, in one embodiment, the cell culture apparatus 10 can include spacer layers for facilitating gas flow.

Gas permeable films for use in the cell culture apparatus 10 can be made from different polymeric materials. The polymers include, for instance, polystyrene, polyethylene, polycarbonate, polyolefin, ethylene vinyl acetate, polymethylpentene, polypropylene, polysulfone, polytetrafluoroethylene (PTFE), or compatible fluoropolymer, a silicone rubber or copolymer, poly(styrene-butadiene-styrene) or combinations of these materials. As manufacturing and compatibility for the growth of cells permits, various polymeric materials may be utilized. Preferably the film is of a thickness that allows for efficient transfer of gas across the film. For example, a polystyrene film may be of a thickness of about 0.003 inches (about 75 micrometers) in thickness, though various thicknesses are also permissive of cell growth. As such, the membrane may be of any thickness, preferably between about 25 and 250 micrometers, or between approximately 25 and 125 micrometers. The membrane allows for the free exchange of gases between the chamber of the assembly and the external environment and may take any size or shape. Preferably, the membrane is durable for manufacture, handling, and manipulation of the apparatus.

The remainder of the cell culture apparatus can be made from, for instance, any suitable polymeric material capable of providing structure to the device. The materials used to form the cell culture apparatus should also be compatible with the cell culture being grown within the apparatus. For instance, the cell culture apparatus can be made from polystyrene, polymethylmethacrylate, polyvinyl chloride, polycarbonate, polysulfone, polystyrene copolymers, fluoropolymers, polyesters, polyamides, polystyrene butadiene copolymers, fully hydrogenated styrenic polymers, polycarbonate PDMS copolymers, and polyolefins such as polyethylene, polypropylene, polymethyl pentene, polypropylene copolymers and cyclic olefin copolymers, and the like.

When using a cell culture apparatus 10 to incubate and grow a cell culture, various different cell culture media need to be fed and removed from the apparatus. For instance, the cell culture apparatus first needs to be inoculated with a cell culture. After the cell culture is fed to the cell culture apparatus 10, depending upon the particular application, various different cell culture media may need to be fed and removed from the apparatus. For instance, in one embodiment, various reagents including cell nutrient compositions may be fed to the cell culture apparatus during the growth of the cell culture. Once the cell culture has grown to the desired extent, the cells are then harvested from the apparatus. In order to harvest the cell culture from the cell culture apparatus, in one embodiment, a proteolytic agent may be fed to the apparatus which causes the cells to detach from walls of the apparatus without harming the cells. The cell culture is then emptied from the apparatus, placed in a bioprocess container, and used as desired.

In order to feed a cell culture media to the cell culture apparatus or in order to remove fluids from the cell culture apparatus, various different manipulations are required including connecting and disconnecting various bioprocess containers. The bioprocess containers can contain a cell culture media that can be fed to the apparatus or can be empty for receiving a fluid from the cell culture apparatus. One aspect of the present disclosure is directed to a method and system for connecting and disconnecting the cell culture apparatus 10 with a bioprocess container.

Figure 2:
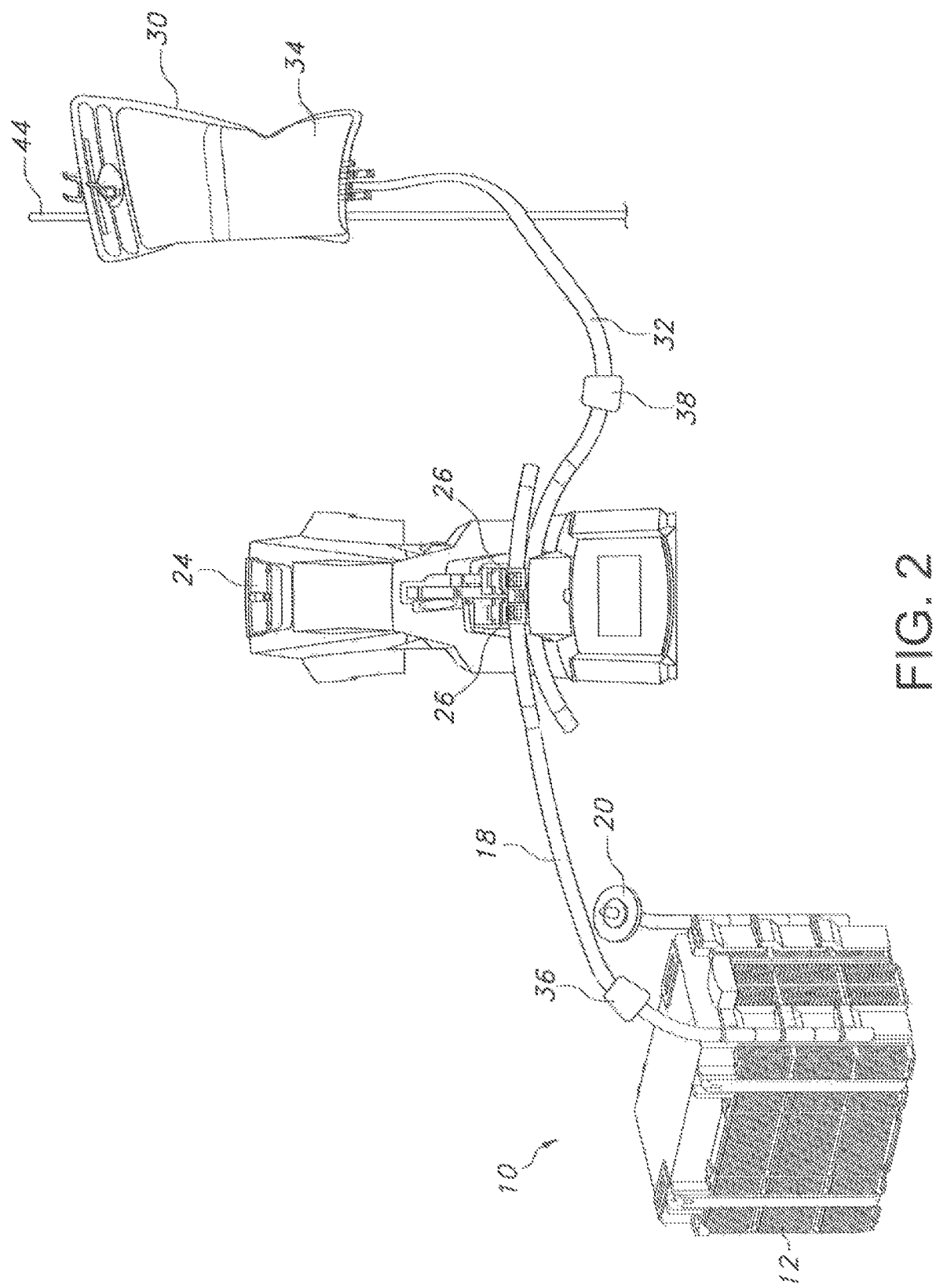
FIG. 2 is perspective view of one embodiment of a cell culture system in accordance with the present disclosure.

Referring to FIG. 2, for instance, one embodiment of a system for connecting the cell culture apparatus 10 with a bioprocess container 30 without producing any open connections is shown. As illustrated, the system further includes a biowelding apparatus 24 that is designed to weld together the bioprocess tube 18 with a cell culture linking tube 32 attached to the bioprocess container 30. The bioprocess container 30 may contain a cell culture media 34. In order to inoculate the cell culture apparatus 10, for instance, the cell culture media 34 may comprise a viable cell culture that is to be fed and loaded into the cell culture apparatus 10. The cells flow into the cell culture apparatus 10 and a certain number of cells flow into each of the cell culture chambers 12. Each cell culture chamber 12 includes a cell growth surface that provides an environment for cell growth and proliferation.

In accordance with the present disclosure, the bioprocess tube 18 and the cell culture linking tube 32 are made from compatible materials and have particular dimensions that have been found to allow the tubes to be welded together without producing an open connection and without risk of ruptures occurring during the welding process. In particular, the bioprocess tube 18 and the cell culture linking tube 32 each have a diameter, a wall thickness, and are made of a thermoplastic elastomer that has been found to provide various advantages and benefits.

More particularly, the bioprocess tube 18 and the cell culture linking tube 32 are made to have a relatively thick wall in conjunction with having a relatively large inside diameter. For example, the bioprocess tube 18 and the cell culture linking tube 32 can have a wall thickness of at least 2.25 mm, such as at least 2.75 mm, such as at least 3 mm. The wall thickness is generally less than about 4.25 mm, such as less than about 3.75 mm, such as less than about 3.5 mm. The inside diameter of each tube is generally greater than about 7.5 mm, such as greater than about 8.5 mm, such as greater than about 9 mm. The inside diameter is generally less than about 12.5 mm, such as less than about 10.5 mm, such as less than about 10 mm. In one embodiment, the dimensions of the bioprocess tube 18 are the same as the dimensions of the cell culture linking tube 32.

The outside diameter of the bioprocess tube and the cell culture linking tube is generally greater than about 13 mm, such as greater than about 14 mm, such as greater than about 15 mm. The outside diameter is generally less than about 20 mm, such as less than about 18 mm, such as less than about 17 mm.

The bioprocess tube 18 and the cell culture linking tube 32 are also made from thermoplastic polymers that are compatible, particularly thermoplastic elastomers that are compatible. For instance, each tube can be made from a silicone polymer. Other elastomers that may be used to produce the tubes include polyvinyl chloride polymers, polypropylene polymers, polyethylene polymers, or a polyester polymer. As used herein, a polymer can refer to a homopolymer, copolymer, a block copolymer, a random copolymer, a terpolymer and the like. In one embodiment, the composition used to make the tubes also includes a plasticizer.

Prior to connecting the bioprocess container 30 to the cell culture apparatus 10, in one embodiment, flow through the cell culture linking tube 32 and the bioprocess tube 18 can be stopped. For instance, the system can include flow stop devices 38 and 36 that can be actuated to prevent flow through the tubes.

Figure 3:
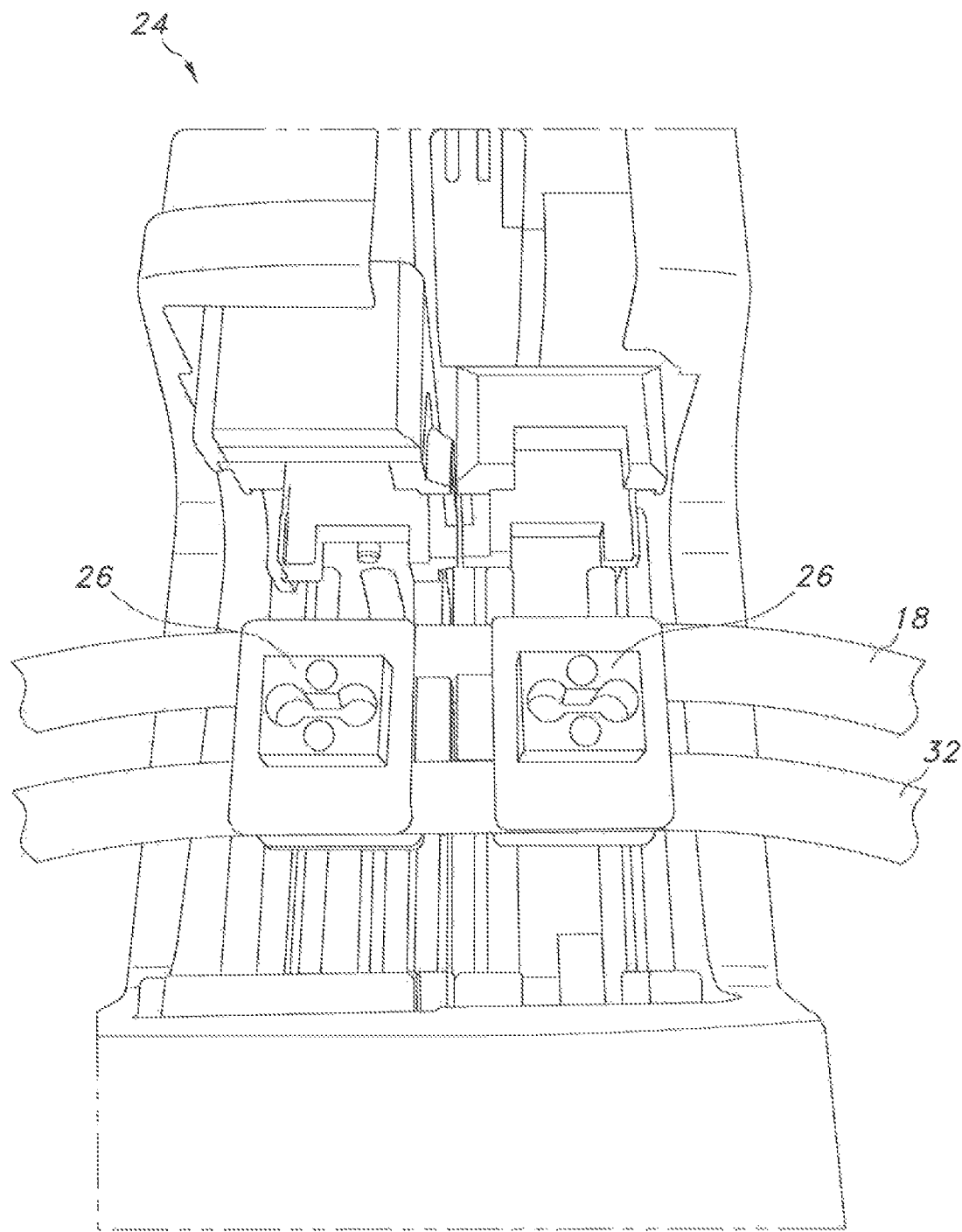
FIG. 3 is a plan view of one embodiment of a biowelding apparatus that may be used in accordance with the present disclosure.

In order to attach the cell culture linking tube 32 to the bioprocess tube 18 in accordance with the present disclosure, the tubes are first loaded into the biowelding apparatus 24. For example, in one embodiment, tube holders 26 can be removed from the biowelding apparatus 24. The bioprocess tube 18 and the cell culture linking tube 32 are then loaded into the biowelding apparatus 24. The tubes are firmly placed in the tube holders 26. As shown in FIGS. 2 and 3, the ends of each tube extend beyond each tube holder 26. Once loaded into the biowelding apparatus 24, both of the tube holders 26 can be closed as shown in FIG. 3.

After the bioprocess tube 18 and the cell culture linking tube 32 are loaded into the biowelding apparatus 24, a blade can be inserted into the biowelding apparatus. The blade, for instance, can have any suitable shape, such as a rectangular shape in the form of a plate. Once the blade is loaded into the biowelding apparatus 24, the cover of the biowelding apparatus is closed and the welding sequence is initiated.

During the welding process, the blade is heated to temperatures sufficient to melt the polymer used to produce the bioprocess tube 18 and the cell culture linking tube 32. For instance, the blade can be heated to a temperature of at least about 280° C., such as at least about 300° C., such as at least about 320° C., such as at least about 340° C., such as at least about 380° C., such as at least about 400° C. The temperature to which the blade is heated depends upon numerous factors including the thermoplastic polymer used to form the tubes. In general, the blade is heated to a temperature of less than about 600° C., such as less than about 500° C., such as less than about 450° C.

Once the blade is heated, the blade is brought into contact with both tubes being held within the tube holder 26. In one embodiment, the blade can be designed to cut both tubes simultaneously. The blade generally has a height that is greater than the outside diameter of the tubes so that after cutting, the tubes remain in contact with the blade in a sealed arrangement. In this manner, the blade is capable of cutting the tubes without creating an open connection. While the tubes are in contact with the blade, the tubes are then rotated by the biowelding apparatus. The blade is then removed from in between the tubes without creating and open connection and while the cut ends of the tubes are in a melted or softened state such that the two tubes become welded together.

Figure 4:
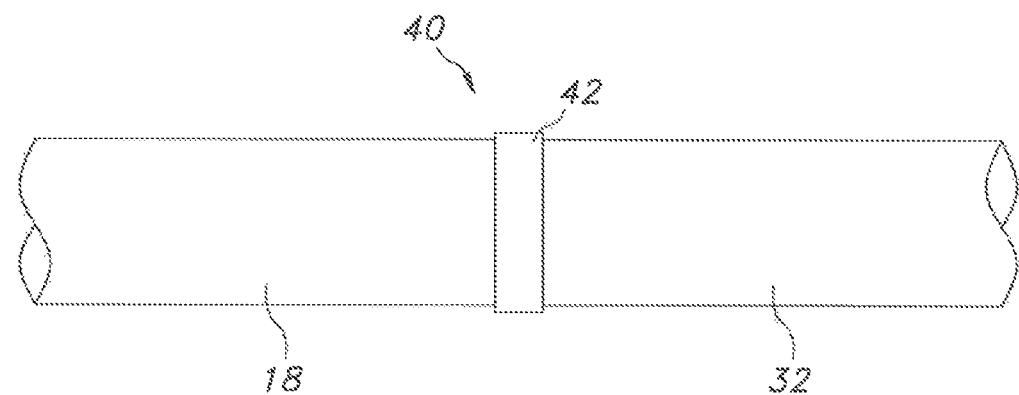
FIG. 4 is a side view of one embodiment of a weld structure between two bioprocessed tubes in accordance with the present disclosure.

In one embodiment, the biowelding apparatus 24 forms a weld structure 40 in between the bioprocess tube 18 and the cell culture linking tube 32 as shown particularly in FIG. 4. The weld structure 40, for instance, can include a leak proof flange 42. For instance, the dimensions of the bioprocess tube, the dimensions of the cell culture linking tube and the thermoplastic elastomers used to form the tubes are selected so that the flange 42 forms during the welding process. The flange 42 ensures not only that a proper weld has occurred but also protects against tube ruptures during the welding process. The flange 42 can be constructed so that it uniformly encircles the bioprocess tube 18 and the cell culture linking tube 32. The flange 42 can also have a height that is relatively uniform around the entire circumference. For instance, the leak proof flange 42 can have a height of greater than about 0.2 mm, such as greater than about 0.5 mm, such as greater than about 0.7 mm, such as greater than about 1 mm, such as greater than about 1.2 mm, such as even greater than about 1.5 mm. The flange generally has a height of less than about 5 mm, such as less than about 3 mm. The height of the flange 42 is, in part, due to the wall thickness of the tubes that are welded together. The wall thickness, for instance, ensures that the tubes weld properly together in a manner such that the tubes are actually aligned.

After the welding process, the weld structure 40 can be inspected by an operator to ensure that a visible flange exists around the circumference of the tubes. The presence of the flange not only indicates radial alignment but also ensures that the tubes are properly welded together. If any irregularities in the weld structure are noted, the welding process can be repeated without producing an open connection. If through visible inspection, the weld structure appears uniform and has integrity, then the welded tubes can be removed from the biowelding apparatus and the flow stop devices 36 and 38 can be opened for allowing fluid to flow from the bioprocess container 30 into the cell culture apparatus 10.

As shown in FIG. 2, the bioprocess container 30 can be suspended from a frame 44 so that gravity can assist in draining the cell culture media 34 into the cell culture apparatus 10.

Figure 5:
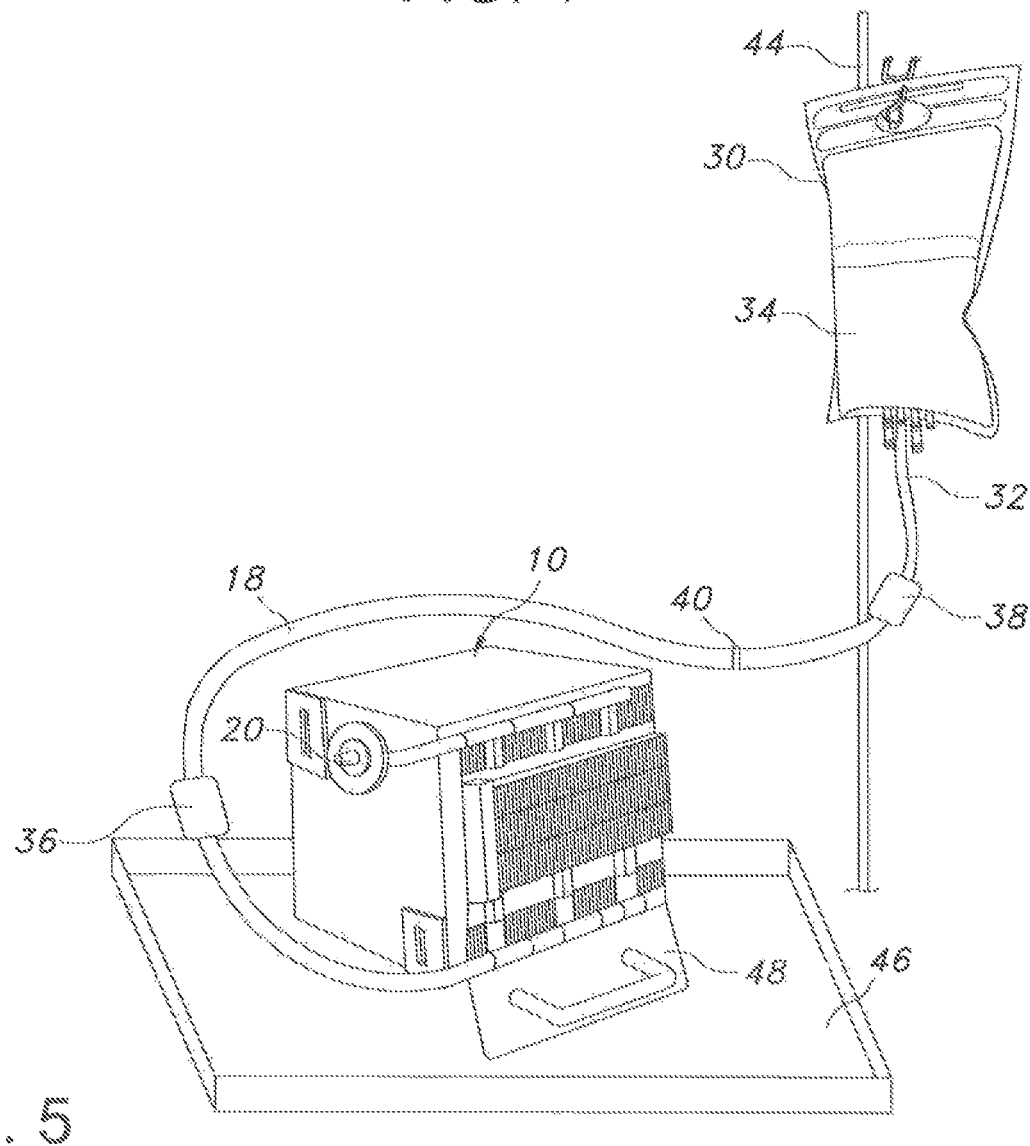
FIG. 5. is a perspective view illustrating a bioprocess container connected to a cell culture apparatus in accordance with the present disclosure.

Referring to FIG. 5, the bioprocess container 30 is shown connected to the cell culture apparatus 10 via the cell culture linking tube 32 and the bioprocess tube 18. In one embodiment, the cell culture apparatus 10 and the bioprocess container 30 can be placed on a rolling cart 46. The bioprocess container 30 can be suspended from a frame 44 that is connected to the cart 46. In this manner, gravity can be used to allow the cell culture media 34 to drain into the cell culture apparatus 10. As shown in FIG. 5, cell culture apparatus 10 can be placed on a wedge member 48 in order to assist in manipulating the cell culture apparatus 10 for removing air bubbles that may exist in the apparatus during loading of the cell culture media 34.

After the cell culture apparatus 10 is inoculated with a cell culture, the cell culture apparatus 10 can be placed in an incubator to allow cell growth on the growth surfaces within the apparatus. During the cell growth process, it may be necessary to extract spent cell culture media and/or insert fresh cell culture media into the cell culture apparatus 10. The new cell culture media, for instance, may comprise any suitable reagent and/or cell nutrient composition. In order to remove a cell culture media from a cell culture apparatus or in order to feed new cell culture media to a cell culture apparatus, a new bioprocess container may need to be attached to the apparatus. In accordance with the present disclosure, the new bioprocess container can be in communication with a cell culture linking tube as described above and the bioprocess container can be placed in fluid communication with the cell culture apparatus repeating the above process in which the cell culture linking tube is welded to the bioprocess tube. In one embodiment, in order to remove cell culture media from the cell culture apparatus, an empty bioprocess container may be connected to the cell culture apparatus using the process as described above.

After the cell culture within the cell culture apparatus has been incubated for a period of time, in one embodiment, it may be desirable to harvest the cells from the apparatus. In order to harvest the cell culture from the cell culture apparatus 10, a proteolytic agent may be fed to the cell culture apparatus. The proteolytic agent, for instance, comprises a chemical composition capable of causing the cells to detach from the surfaces of the cell culture apparatus without harming the cells. In one embodiment, the proteolytic agent may comprise an enzymatic additive. The enzymatic additive, for instance, may comprise any suitable protease, such as trypsin, pronase, collagenase, and/or proteinse K.

In one embodiment, the proteolytic agent can be fed to the cell culture apparatus at a neutral pH or at a pH above the pH of the normal culture conditions. For example, the pH can be anywhere from about 7 to about 10, such as from about 7.8 to about 9.5. If desired, any liquids contained in the cell culture apparatus, such as a growth medium, can be removed and separated from the cell culture prior to feeding the proteolytic agent to the apparatus. If desired, the cell culture can also be rinsed prior to feeding the proteolytic agent to the cell culture apparatus. For instance, the cell culture can be rinsed with an aqueous isotonic buffer.

The proteolytic agent is generally added to the cell culture apparatus in the form of a liquid. In addition to the proteolytic agent, the proteolytic composition may contain various other ingredients and components. In one embodiment, for instance, the proteolytic agent can be present in conjunction with a chelating agent such as EDTA. The chelating agent acts as a scavenger for cations that may be present in the cell culture apparatus. Such cations can include, for instance, calcium, magnesium, and the like. The proteolytic agent can be contained in the proteolytic composition at a concentration of generally greater than about 0.1%, such as greater than about 0.2%. The concentration of the proteolytic agent in the composition is generally less than about 0.5%, such as less than about 0.3%, such as less than about 0.2%.

In order to feed the proteolytic agent, such as trypsin, into the cell culture apparatus 10, a bioprocess container containing the proteolytic agent is connected to the bioprocess apparatus using the welding process as described above. In one embodiment, in addition to a proteolytic agent, a quench composition is also fed to the cell culture apparatus for harvesting the cells. The proteolytic agent releases the cells from the growth surfaces in the cell culture apparatus, while the quench composition is added in order to stop the enzymatic reaction. After the proteolytic agent and the quench composition have been feed into the cell culture apparatus, the entire contents of the cell culture apparatus can be drained into the bioprocess container that supplied the quench composition or can be drained into an empty bioprocess container.

Figure 6:
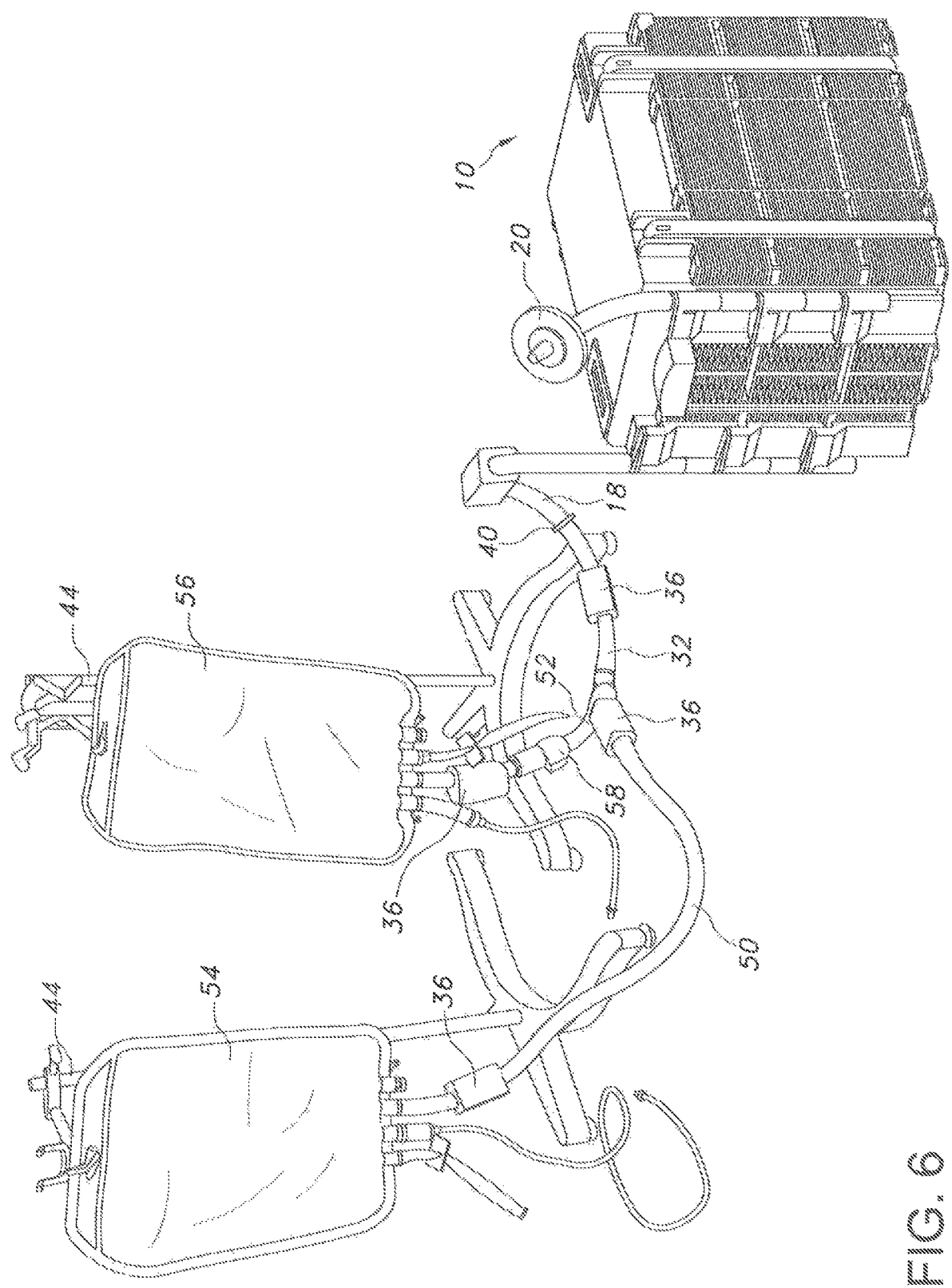
FIG. 6 is a perspective view of one embodiment of a system for harvesting cell cultures from a cell culture apparatus.

Referring to FIG. 6, one embodiment of a system made in accordance with the present disclosure for harvesting cells from a cell culture apparatus is shown. The system includes a cell culture apparatus 10 in fluid communication with a bioprocess tube 18. The bioprocess tube 18 has been welded in accordance with the present disclosure with a cell culture linking tube 32. As shown, a weld structure 40 comprising a leak proof flange divides the bioprocess tube 18 from the cell culture linking tube 32.

The cell culture linking tube 32 is in fluid communication with a first Y tube 50 and a second Y tube 52 via a Y structure. The first Y tube 50 is in fluid communication with a first bioprocess container 54, while the second Y tube 52 is in communication with a second bioprocess container 56.

The first bioprocess container 54 is configured to contain a proteolytic composition for feeding to the cell culture apparatus 10. The second bioprocess container 56, on the other hand, is designed to contain a quench composition that is also to be fed to the cell culture apparatus 10 typically after the proteolytic composition. In order to control the flow of fluids through the system, each of the tubes are in communication with a flow stop device 36.

In order to harvest the cells using the system illustrated in FIG. 6, the first and second bioprocess containers are first connected to the bioprocess apparatus 10 through the process of the present disclosure as discussed above. The proteolytic composition contained in the first bioprocess container 54 is then feed to the cell culture apparatus 10. After the proteolytic composition is feed to the cell culture apparatus, a quench composition contained in the second bioprocess container 56 is fed to the cell culture apparatus 10. After the quench composition is fed to the cell culture apparatus 10, the cell culture apparatus 10 is then drained into the second bioprocess container 56. The flow stop devices 36 can be used to stop and start flow from the bioprocess containers in to and out of the cell culture apparatus. As shown in FIG. 6, the second Y tube 52 includes a quick disconnect device 58. Once the cell culture is collected in the second bioprocess container 56, the quick disconnect device 58 is engaged for disconnecting the bioprocess container from the system. The bioprocess container 56 can then be used to store and transport the cell culture.

In addition to a system and method for incubating, growing and harvesting cell cultures, the present disclosure is also directed to a bioprocess container particularly well suited for use in the process and system of the present disclosure. For example, referring to FIGS. 7 through 14, various embodiments of a bioprocess container 30 are shown. In one embodiment, the bioprocess container 30 can be made from a flexible polymer film. The polymer film may be, for instance, a single layer film or a multilayer film. Polymers that may be used to produce the container include, for instance, polyvinyl chloride, polyolefin polymers such as polypropylene and/or polyethylene, polyester polymers, and the like. In one embodiment, the bioprocess container 30 is transparent or translucent so that the contents of the container can be viewed. The bioprocess container can generally have a volume of greater than about 0.5 liters, such as greater than about 0.75 liters. The volume of the container is generally less than about 25 liters, such as less than about 15 liters, such as less than about 10 liters, such as less than about 5 liters, such as less than about 3 liters, such as less than about 2 liters, such as less than about 1.5 liters.

Figure 7:
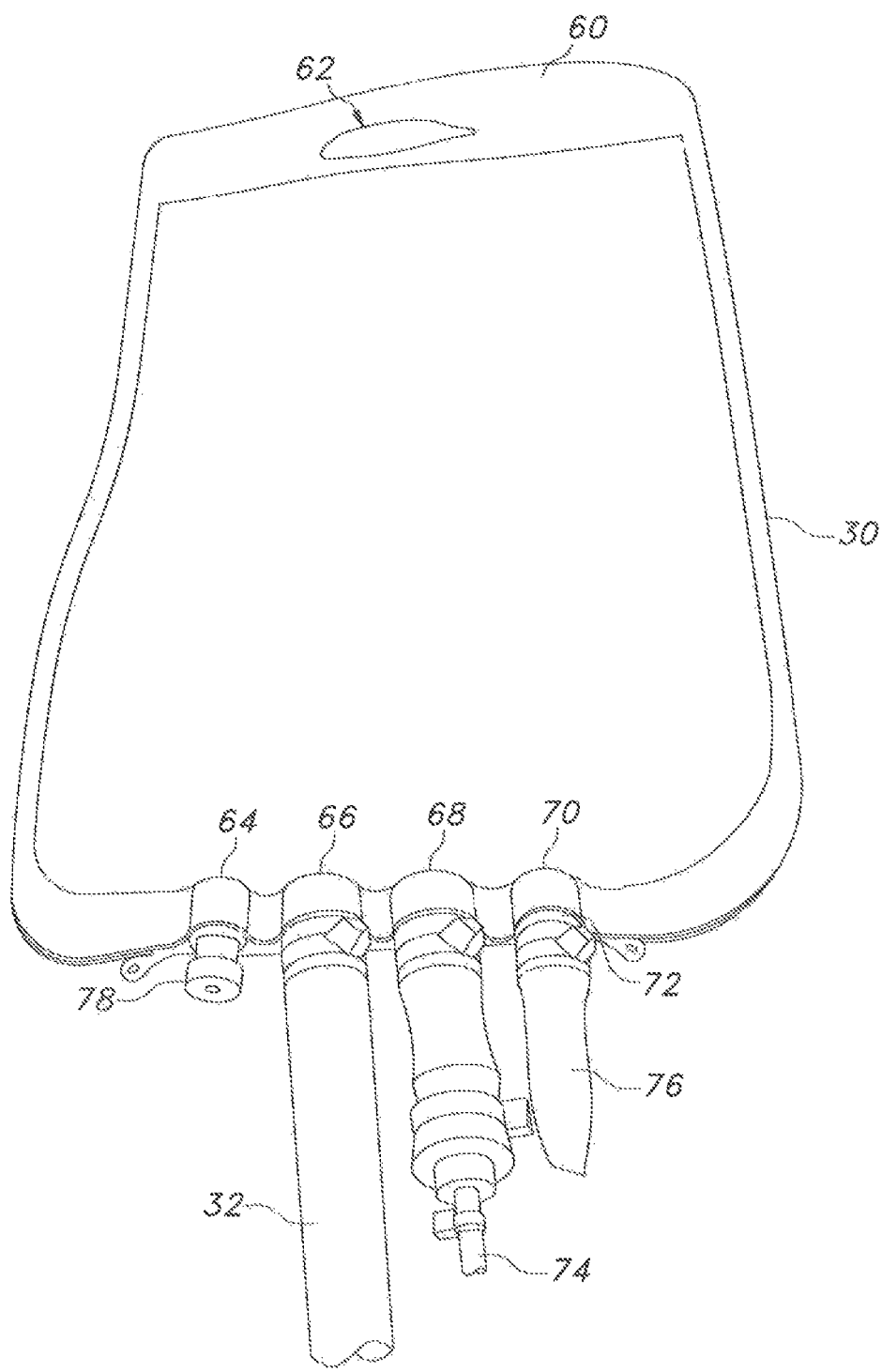
FIG. 7 is a perspective view of one embodiment of a bioprocess container in accordance with the present disclosure.
Figure 8:
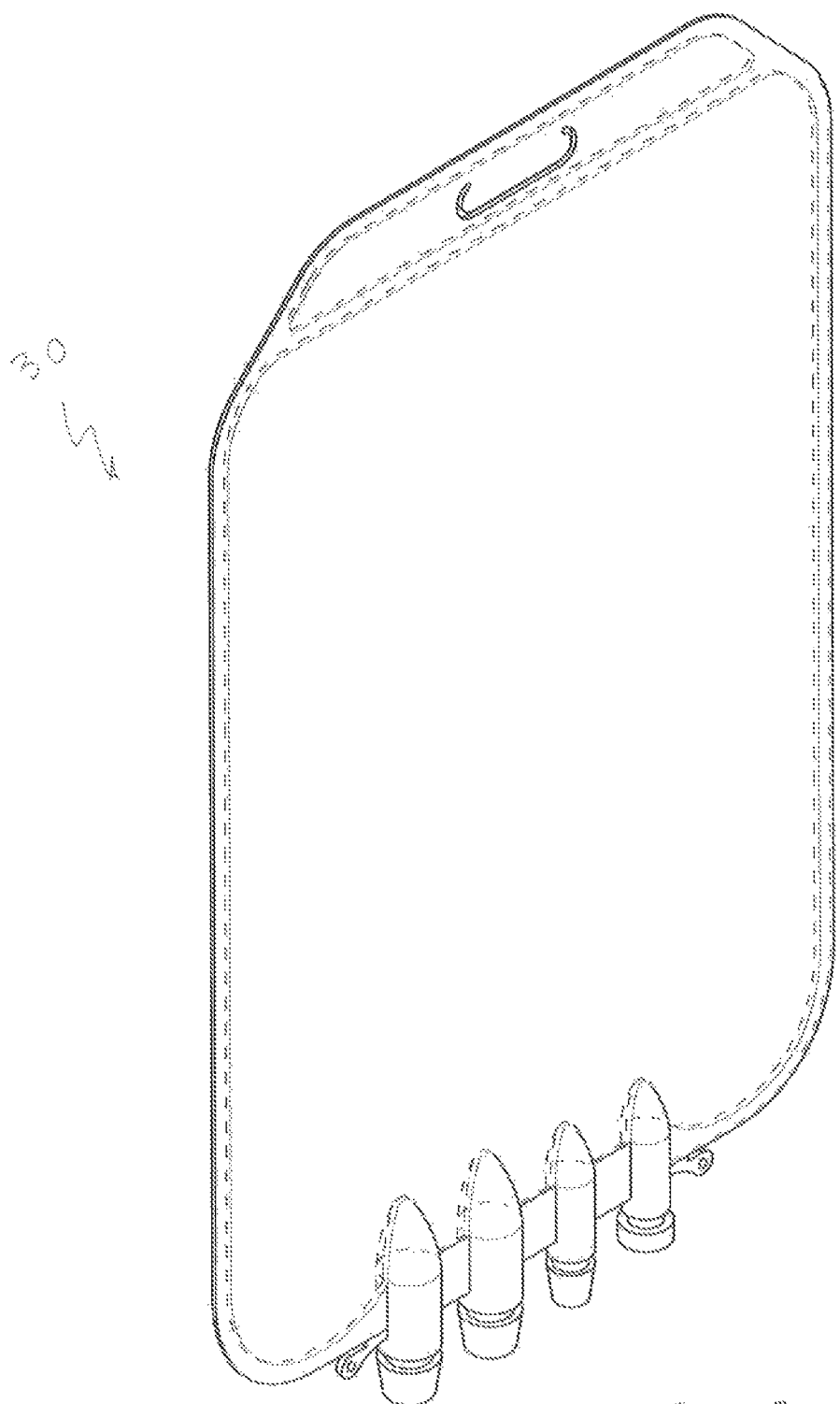
FIG. 8. is a perspective view of one embodiment of a bioprocess container in accordance with the present disclosure illustrating a unique and ornamental design.
Figure 9:
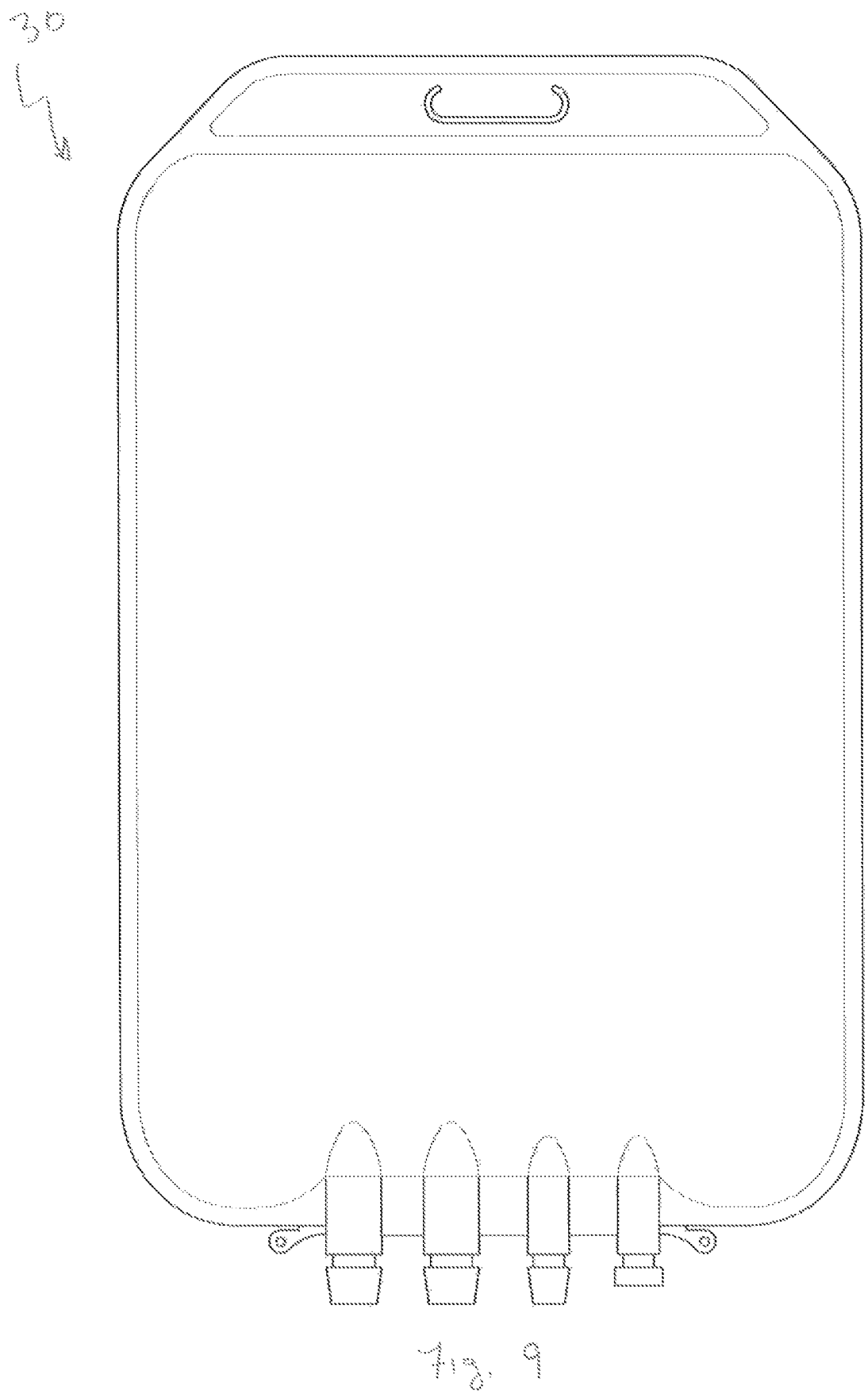
FIG. 9 is a side view of the bioprocess container illustrated in FIG. 8.
Figure 10:
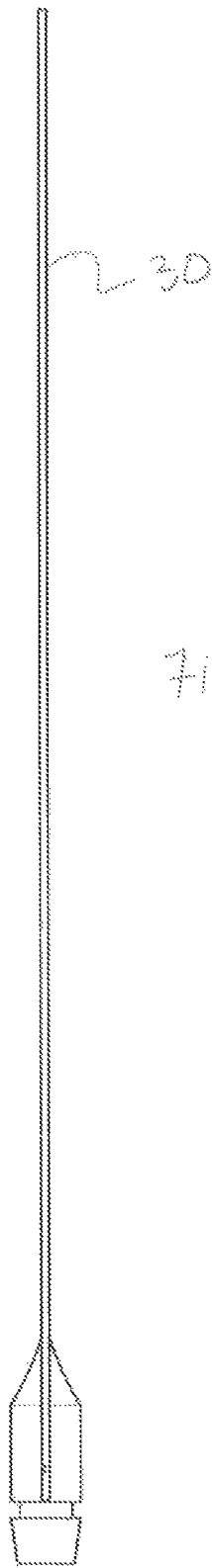
FIG. 10 is another side view of the bioprocess container illustrated in FIG. 8.
Figure 11:
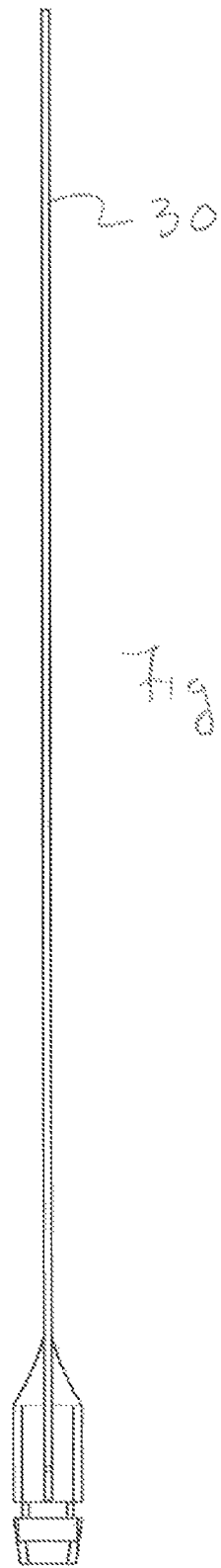
FIG. 11 is another side view of the bioprocess container illustrated in FIG. 8 showing the side opposite to the side illustrated in FIG. 10.
Figure 12:
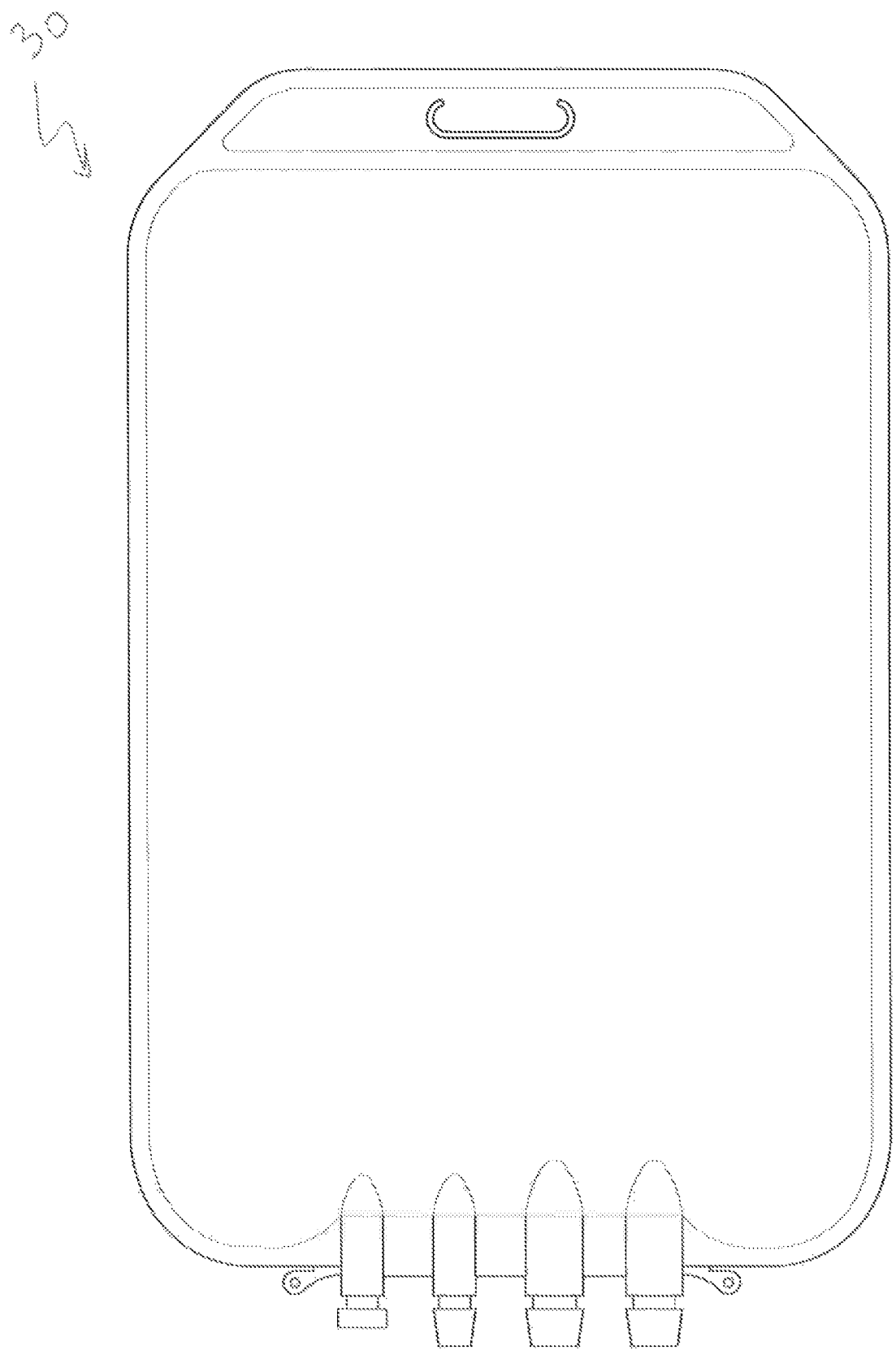
FIG. 12 is another side view of the bioprocess container illustrated in FIG. 8 showing the opposite side of the container from FIG. 9.
Figure 13:
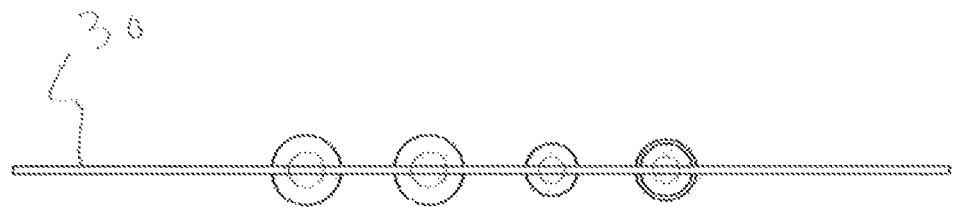
FIG. 13 is top view of the bioprocess container illustrated in FIG. 8.
Figure 14:
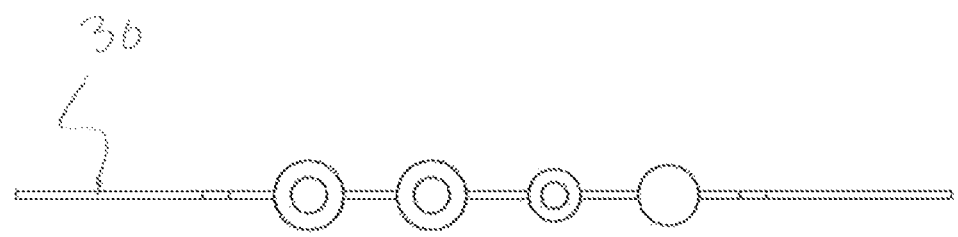
FIG. 14 is bottom view of the bioprocess container illustrated in FIG. 8.

The bioprocess container 30 as shown FIG. 7 can include a first end that includes a tab portion 60. The tab portion 60 is for holding and manipulating the bioprocess container 30. In one embodiment, the tab portion 60 can include an opening 62 that can service as a handle and/or can be used to suspend the bioprocess container from a clamp or other similar holding device.

The opposite end of the bioprocess container 30 includes a plurality of ports. The bioprocess container, for instance, can include at least one port, such at least two ports, such as at least 3 ports. In general, the bioprocess container 30 contains less than about 6 ports, such as less than about 5 ports, such as less than about 4 ports. In the embodiment illustrated in FIG. 7, the bioprocess container includes 4 ports 64, 66, 68 and 70. In accordance with the present disclosure, the bioprocess container 30 further includes a flow guiding device 72 that defines the ports 64, 66, 68 and 70. The flow guiding device 72 is a single structure that can be made from a rigid material, such as a rigid plastic. The flow guiding device 72 provides numerous advantages and benefits when handling and manipulating the bioprocess container 30. The flow guiding device 72, for instance, facilitates connection of the bioprocess container to various tubes and other outlets. In addition, the flow guiding device 72 prevents kinks and other flow blockages that may otherwise occur. These advantages are obtained because the flow guiding device is not only made from a single piece of material but also includes internal diameters that are relatively large in comparison to past bioprocess containers. For instance, the internal diameter of each port 64, 66, 68 and 70 can be greater than about 6 mm, such as greater than about 6.5 mm, such as greater than about 7 mm, such as greater than about 7.5 mm, such as greater than about 8 mm, such as greater than about 8.5 mm, such as greater than about 9 mm. The inside diameter of each port within the flow guiding device 72 is generally less than about 14 mm, such as less than about 12 mm, such as less than about 10 mm. As shown particularly in FIG. 7, the ports are spaced apart so that the different tubes, inlets and outlets do not interfere with each other. The spacing between each port, for instance, can generally be greater than about 3 mm, such as greater than about 4 mm, such as greater than about 5 mm, such as greater than about 6 mm, such as greater than about 7 mm, such as greater than about 8 mm, such as greater than about 9 mm, such as greater than about 10 mm. The spacing between each port is generally less than about 50 mm, such as less than about 40 mm, such as less than about 30 mm, such as less than about 20 mm, such as less than about 10 mm, such as less than about 8 mm, such as less than about 6 mm.

In the embodiment illustrated in FIG. 7, the bioprocess container 30 includes 4 ports 64, 66, 68 and 70. Port 66 is connected to the cell culture linking tube 32 as described above. The cell culture linking tube has physical dimensions and properties that allow for the tube to be successfully welded with another tube having similar dimensions and properties. As described above, the dimensions and properties of the cell culture linking tube 32 allows for the bioprocess container 30 to be connected to a cell culture apparatus without creating an open connection. Thus, the bioprocess container 30 can be connected and disconnected from a cell culture apparatus without having to complete the operation under a fume hood or in a controlled environment with extensive monitoring.

In addition to port 66, the bioprocess container 30 includes a port 68 attached to a sampling line 74. The sampling 74 can be used to obtain samples from the bioprocess container. Port 70, on the other hand, is connected to a fill line 76. Port 70 and fill line 76 can be used to fill the bioprocess container with a cell culture media.

Finally, the bioprocess container 30 includes a fourth port 64. The fourth port 64 is connected to an injection port 78. The injection port 78 can be designed to allow a user to inject small amounts of material into the bioprocess container 30. For instance, the injection port 78 can be used to inject viable cells into the bioprocess container 30 if desired. The injection port 78 can also be used to alter properties of the cell culture media such as pH. The injection port 78 can also be used to combine a cell culture media contained within the bioprocess container 30 with other additives and components.

The devices, facilities and methods described herein are suitable for culturing any desired cell line, including prokaryotic and/or eukaryotic cell lines. Further, in embodiments, the devices, facilities and methods are suitable for filtering fluids during the culturing of suspension cells or anchorage-dependent (adherent) cells and are suitable for production operations configured for production of pharmaceutical and biopharmaceutical products—such as polypeptide products, nucleic acid products (for example DNA or RNA), or cells and/or viruses such as those used in cellular and/or viral therapies.

In embodiments, the cells express or produce a product, such as a recombinant therapeutic or diagnostic product. As described in more detail below, examples of products produced by cells include, but are not limited to, antibody molecules (e.g., monoclonal antibodies, bispecific antibodies), antibody mimetics (polypeptide molecules that bind specifically to antigens but that are not structurally related to antibodies such as e.g. DARPins, affibodies, adnectins, or IgNARs), fusion proteins (e.g., Fc fusion proteins, chimeric cytokines), other recombinant proteins (e.g., glycosylated proteins, enzymes, hormones), viral therapeutics (e.g., anticancer oncolytic viruses, viral vectors for gene therapy and viral immunotherapy), cell therapeutics (e.g., pluripotent stem cells, mesenchymal stem cells and adult stem cells), vaccines or lipid-encapsulated particles (e.g., exosomes, virus-like particles), RNA (such as e.g. siRNA) or DNA (such as e.g. plasmid DNA), antibiotics or amino acids. In embodiments, the devices, facilities and methods can be used for producing biosimilars.

As mentioned, in embodiments, devices, facilities and methods allow for the production of eukaryotic cells, e.g., mammalian cells or lower eukaryotic cells such as for example yeast cells or filamentous fungi cells, or prokaryotic cells such as Gram-positive or Gram-negative cells and/or products of the eukaryotic or prokaryotic cells, e.g., proteins, peptides, antibiotics, amino acids, nucleic acids (such as DNA or RNA), synthesised by the eukaryotic cells in a large-scale manner. Unless stated otherwise herein, the devices, facilities, and methods can include any desired volume or production capacity including but not limited to bench-scale, pilot-scale, and full production scale capacities.

Moreover and unless stated otherwise herein, the devices, facilities, and methods can include any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermentor or fermentation unit, or any other reaction vessel and the term "reactor" is used interchangeably with "fermentor." For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and CO2 levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reacotrs within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316L or any other suitable stainless steel) and Inconel, plastics, and/or glass.

In embodiments and unless stated otherwise herein, the devices, facilities, and methods described herein can also include any suitable unit operation and/or equipment not otherwise mentioned, such as operations and/or equipment for separation, purification, and isolation of such products. Any suitable facility and environment can be used, such as traditional stick-built facilities, modular, mobile and temporary facilities, or any other suitable construction, facility, and/or layout. For example, in some embodiments modular clean-rooms can be used. Additionally and unless otherwise stated, the devices, systems, and methods described herein can be housed and/or performed in a single location or facility or alternatively be housed and/or performed at separate or multiple locations and/or facilities.

By way of non-limiting examples and without limitation, U.S. Publication Nos. 2013/0280797; 2012/0077429; 2011/0280797; 2009/0305626; and U.S. Pat. Nos. 8,298,054; 7,629,167; and 5,656,491, which are hereby incorporated by reference in their entirety, describe example facilities, equipment, and/or systems that may be suitable.

In embodiments, the cells are eukaryotic cells, e.g., mammalian cells. The mammalian cells can be for example human or rodent or bovine cell lines or cell strains. Examples of such cells, cell lines or cell strains are e.g. mouse myeloma (NSO)-cell lines, Chinese hamster ovary (CHO)-cell lines, HT1080, H9, HepG2, MCF7, MDBK Jurkat, NIH3T3, PC12, BHK (baby hamster kidney cell), VERO, SP2/0, YB2/0, Y0, C127, L cell, COS, e.g., COS1 and COS7, QC1-3, HEK-293, VERO, PER.C6, HeLA, EBI, EB2, EB3, oncolytic or hybridoma-cell lines. Preferably the mammalian cells are CHO-cell lines. In one embodiment, the cell is a CHO cell. In one embodiment, the cell is a CHO-K1 cell, a CHO-K1 SV cell, a DG44 CHO cell, a DUXB11 CHO cell, a CHOS, a CHO GS knock-out cell, a CHO FUT8 GS knock-out cell, a CHOZN, or a CHO-derived cell. The CHO GS knock-out cell (e.g., GSKO cell) is, for example, a CHO-K1 SV GS knockout cell. The CHO FUT8 knockout cell is, for example, the Potelligent® CHOK1 SV (Lonza Biologics, Inc.). Eukaryotic cells can also be avian cells, cell lines or cell strains, such as for example, EBx® cells, EB14, EB24, EB26, EB66, or EBvl3.

In one embodiment, the eukaryotic cells are stem cells. The stem cells can be, for example, pluripotent stem cells, including embryonic stem cells (ESCs), adult stem cells, induced pluripotent stem cells (iPSCs), tissue specific stem cells (e.g., hematopoietic stem cells) and mesenchymal stem cells (MSCs).

In one embodiment, the cell is a differentiated form of any of the cells described herein. In one embodiment, the cell is a cell derived from any primary cell in culture.

In embodiments, the cell is a hepatocyte such as a human hepatocyte, animal hepatocyte, or a non-parenchymal cell. For example, the cell can be a plateable metabolism qualified human hepatocyte, a plateable induction qualified human hepatocyte, plateable Qualyst Transporter Certified™ human hepatocyte, suspension qualified human hepatocyte (including 10-donor and 20-donor pooled hepatocytes), human hepatic kupffer cells, human hepatic stellate cells, dog hepatocytes (including single and pooled Beagle hepatocytes), mouse hepatocytes (including CD-1 and C57Bl/6 hepatocytes), rat hepatocytes (including Sprague-Dawley, Wistar Han, and Wistar hepatocytes), monkey hepatocytes (including Cynomolgus or Rhesus monkey hepatocytes), cat hepatocytes (including Domestic Shorthair hepatocytes), and rabbit hepatocytes (including New Zealand White hepatocytes). Example hepatocytes are commercially available from Triangle Research Labs, LLC, 6 Davis Drive Research Triangle Park, N.C., USA 27709.

In one embodiment, the eukaryotic cell is a lower eukaryotic cell such as e.g. a yeast cell (e.g., *Pichia* genus (e.g. *Pichia pastoris. Pichia methanolica, Pichia kluyveri*, and *Pichia angusta*), *Komagataella* genus (e.g. *Komagataella pastoris, Komagataella pseudopastoris* or *Komagataella phaffii*), *Saccharomyces* genus (e.g. *Saccharomyces cerevisae, cerevisiae, Saccharomyces kluyveri, Saccharomyces uvarum*), *Kluyveromyces* genus (e.g. *Kluyveromyces lactis, Kluyveromyces marxianus*), the *Candida* genus (e.g. *Candida utilis, Candida cacaoi, Candida boidinii*), the *Geotrichum* genus (e.g. *Geotrichum fermentans*), *Hansenula polymorphs, Yarrowia lipolytica*, or *Schizosaccharomyces pombe*. Preferred is the species *Pichia pastoris*. Examples for *Pichia pastoris* strains are X33, GS115, KM71, KM71H; and CBS7435.

In one embodiment, the eukaryotic cell is a fungal cell (e.g. *Aspergillus* (such as *A. niger, A. fumigatus, A. orzyae, A. nidula*), *Acremonium* (such as *A. thermophilum*), *Chaetomium* (such as *C. thermophilum*), *Chrysosporium* (such as *C. thermophile*), *Cordyceps* (such as *C. militaris*), *Corynascus, Ctenomyces, Fusarium* (such as *F. oxysporum*), *Glomerella* (such as *G. graminicola*), *Hypocrea* (such as *H. jecorina*), *Magnaporthe* (such as *M. orzyae*), *Myceliophthora* (such as *M. thermophile*), *Nectria* (such as *N. heamatococca*), *Neurospora* (such as *N. crassa*), *Penicillium, Sporotrichum* (such as *S. thermophile*), *Thielavia* (such as *T. terrestris, T. heterothallica*), *Trichoderma* (such as *T. reesei*), or *Verticillium* (such as *V. dahlia*)).

In one embodiment, the eukaryotic cell is an insect cell (e.g., Sf9, Mimic™ Sf9, Sf21, High Five™ (BT1-TN-5B1-4), or BT1-Ea88 cells), an algae cell (e.g., of the genus *Amphora, Bacillariophyceae, Dunaliella, Chlorella, Chiamydomonas, Cyanophyta* (cyanobacteria), *Nannochloropsis, Spirulina,* or *Ochromonas*), or a plant cell (e.g., cells from monocotyledonous plants (e.g., maize, rice, wheat, or Setaria), or from a dicotyledonous plants (e.g., cassava, potato, soybean, tomato, tobacco, alfalfa, *Physcomitrella patens* or *Arabidopsis*).

In one embodiment, the cell is a bacterial or prokaryotic cell.

In embodiments, the prokaryotic cell is a Gram-positive cells such as *Bacillus, Streptomyces Streptococcus, Staphylococcus* or *Lactobacillus*. *Bacillus* that can be used is, e.g. the *B. subtilis, B. amyloliquefaciens, B. licheniformis, B. natto,* or *B. megaterium*. In embodiments, the cell is *B. subtilis,* such as *B. subtilis* 3NA and *B. subtilis* 168. *Bacillus* is obtainable from, e.g., the *Bacillus* Genetic Stock Center, Biological Sciences 556, 484 West 12$^{th}$ Avenue, Columbus Ohio 43210-1214.

In one embodiment, the prokaryotic cell is a Gram-negative cell, such as *Salmonella* spp. or *Escherichia coli*, such as e.g., TG1, TG2, W3110, DH1, DHB4, DH5a, HMS 174, HMS174 (DE3), NM533, C600, HB101, JM109, MC4100, XL1-Blue and Origami, as well as those derived from *E. coli* B-strains, such as for example BL-21 or BL21 (DE3), all of which are commercially available.

Suitable host cells are commercially available, for example, from culture collections such as the DSMZ (Deutsche Sammlung von Mikroorganismen and Zellkulturen GmbH, Braunschweig, Germany) or the American Type Culture Collection (ATCC).

In embodiments, the cultured cells are used to produce proteins e.g., antibodies, e.g., monoclonal antibodies, and/or recombinant proteins, for therapeutic use. In embodiments, the cultured cells produce peptides, amino acids, fatty acids or other useful biochemical intermediates or metabolites. For example, in embodiments, molecules having a molecular weight of about 4000 daltons to greater than about 140,000 daltons can be produced. In embodiments, these molecules can have a range of complexity and can include posttranslational modifications including glycosylation.

In embodiments, the protein is, e.g., BOTOX, Myobloc, Neurobloc, Dysport (or other serotypes of botulinum neurotoxins), alglucosidase alpha, daptomycin, YH-16, choriogonadotropin alpha, filgrastim, cetrorelix, interleukin-2, aldesleukin, teceleulin, denileukin diftitox, interferon alpha-n3 (injection), interferon alpha-nl, DL-8234, interferon, Suntory (gamma-1a), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alpha, collagenase, carperitide, recombinant human epidermal growth factor (topical gel, wound healing), DWP401, darbepoetin alpha, epoetin omega, epoetin beta, epoetin alpha, desirudin, lepirudin, bivalirudin, nonacog alpha, Mononine, eptacog alpha (activated), recombinant Factor VIII+VWF, Recombinate, recombinant Factor VIII, Factor VIII (recombinant), Alphnmate, octocog alpha, Factor VIII, palifermin, Indikinase, tenecteplase, alteplase, pamiteplase, reteplase, nateplase, monteplase, follitropin alpha, rFSH, hpFSH, micafungin, pegfilgrastim, lenograstim, nartograstim, sermorelin, glucagon, exenatide, pramlintide, iniglucerase, gaisulfase, Leucotropin, molgramostim, triptorelin acetate, histrelin (subcutaneous implant, Hydron), deslorelin, histrelin, nafarelin, leuprolide sustained release depot (ATRIGEL), leuprolide implant (DUROS), goserelin, Eutropin, KP-102 program, somatropin, mecasermin (growth failure), enlfavirtide, Org-33408, insulin glargine, insulin glulisine, insulin (inhaled), insulin lispro, insulin deternir, insulin (buccal. RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, dornase alpha, trafermin, ziconotide, taltirelin, diboterminalfa, atosiban, becaplermin, eptifibatide, Zemaira, CTC-111, Shanvac-B, HPV vaccine (quadrivalent), octreotide, lanreotide, ancestirn, agalsidase beta, agalsidase alpha, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-21S, vapreotide, idursulfase, omnapatrilat, recombinant serum albumin, certolizumab pegol, glucarpidase, human recombinant C1 esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexigananacetate, ADI-PEG-20, LDI-200, degarelix, cintredelinbesudotox, Favld, MDX-1379, ISAtx-247, liraglutide, teriparatide (osteoporosis), tifacogin, AA4500, T4N5 liposome lotion, catumaxomab, DWP413, ART-123, Chrysalin, desmoteplase, amediplase, corifollitropinaipha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alpha-n3 (oral), belatacept, transdermal insulin patches, AMG-531, MBP-8298, Xerecept, opebacan, AID-SVAX, GV-1001, LymphoScan, ranpirnase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-1 (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, rornidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, ovarian cancer immunotherapeutic vaccine, SB-249553, Oncovax-CL, OncoVax-P, BLP-25, CerVax-16, multi-epitope peptide melanoma vaccine (MART-1, gp100, tyrosinase), nemifitide, rAAT (inhaled), rAAT (dermatological), CGRP (inhaled, asthma), pegsunercept, thymosinbeta4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 131I-TM-601, KK-220, T-10, ularitide, depelestat, hematide, Chrysalin (topical), rNAPc2, recombinant Factor V111 (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, ACM-9604, linaclotid eacetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutaneous injection, eczema), pitrakinra (inhaled dry powder, asthma), Multikine, RG-1068, MM-093, NBI-6024, AT-001, PI-0824, Org-39141, Cpn10 (autoimmune diseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alpha-n3 (topical), 1RX-3, RDP-58, Tauferon, bile salt stimulated lipase, Merispase, alaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, malaria vaccine (virosomes, PeviPRO), ALTU-135, parvovirus B19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93.02, MTB72F vaccine (tuberculosis), MVA-Ag85A vaccine (tuberculosis), FARA04, BA-210, recombinant plague FIV vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, HA, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3SSIL-3, TST-10088, PRO-1762, Combotox, cholecystokinin-B/gastrin-receptor binding peptides, 111In-hEGF, AE-37, trasnizumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1100 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV4710, ALG-889, Org-41259, rhCC10, F-991, thymopentin (pulmonary diseases), r(m)CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OS1, AC-162352, PRX-302, LFn-p24 fusion vaccine (Therapore), EP-1043, *S pneumoniae* pediatric vaccine, malaria vaccine, *Neisseria meningitidis* Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH(1-34) (transdermal, ViaDerm), 768974, SYN-101, PGN-0052, aviscumnine, BIM-23190, tuberculosis vaccine, multi-epitope tyrosinase peptide, cancer vaccine, enkastim, APC-8024, GI-5005, ACC-001, TTS-CD3, vascular-targeted TNF (solid tumors), desmopressin (buccal controlled-release), onercept, and TP-9201.

In some embodiments, the polypeptide is adalimumab (HUMIRA), infliximab (REMICADE™), rituximab (RITUXAN™/MAB THERA™) etanercept (ENBREL™), bevacizumab (AVASTIN™), trastuzumab (HERCEPTIN™), pegrilgrastim (NEULASTA™), or any other suitable polypeptide including biosimilars and biobetters.

Other suitable polypeptides are those listed below and in Table 1 of US2016/0097074:

TABLE I

| Protein Product | Reference Listed Drug |
|---|---|
| interferon gamma-1b | Actimmune ® |
| alteplase; tissue plasminogen activator | Activase ®/Cathflo ® |
| Recombinant antihemophilic factor | Advate |
| human albumin | Albutein ® |
| Laronidase | Aldurazyme ® |
| Interferon alfa-N3, human leukocyte derived | Alferon N ® |
| human antihemophilic factor | Alphanate ® |
| virus-filtered human coagulation factor IX | AlphaNine ® SD |
| Alefacept; recombinant, dimeric fusion protein LFA3-Ig | Amevive ® |
| Bivalirudin | Angiomax ® |
| darbepoetin alfa | Aranesp ™ |
| Bevacizumab | Avastin ™ |
| interferon beta-1a; recombinant | Avonex ® |
| coagulation factor IX | BeneFix ™ |
| Interferon beta-1b | Betaseron ® |
| Tositumomab | BEXXAR ® |
| antihemophilic factor | Bioclate ™ |
| human growth hormone | BioTropin ™ |
| botulinum toxin type A | BOTOX ® |
| Alemtuzumab | Campath ® |
| acritumomab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune fab [ovine] | DigiFab ™ |
| Rasburicase | Elitek ® |
| Etanercept | ENBREL ® |
| epoietin alfa | Epogen ® |
| Cetuximab | Erbitux ™ |
| algasidase beta | Fabrazyme ® |
| Urofollitropin | Fertinex ™ |
| follitropin beta | Follistim ™ |
| Teriparatide | FORTEO ® |
| human somatropin | GenoTropin ® |
| Glucagon | GlucaGen ® |
| follitropin alfa | Gonal-F ® |
| antihemophilic factor | Helixate ® |
| Antihemophilic Factor; Factor XIII | HEMOFIL |
| adefovir dipivoxil | Hepsera ™ |
| Trastuzumab | Herceptin ® |
| Insulin | Humalog ® |
| antihemophilic factor/von Willebrand factor complex-human | Humate-P ® |
| Somatotropin | Humatrope ® |
| Adalimumab | HUMIRA ™ |
| human insulin | Humulin ® |
| recombinant human hyaluronidase | Hylenex ™ |
| interferon alfacon-1 | Infergen ® |
| eptifibatide | Integrilin ™ |
| alpha-interferon | Intron A ® |
| Palifermin | Kepivance |
| Anakinra | Kineret ™ |
| antihemophilic factor | Kogenate ® FS |
| insulin glargine | Lantus ® |
| granulocyte macrophage colony-stimulating factor | Leukine ®/Leukine ® Liquid |
| lutropin alfa for injection | Luveris |
| OspA lipoprotein | LYMErix ™ |
| Ranibizumab | LUCENTIS ® |
| gemtuzumab ozogamicin | Mylotarg ™ |
| Galsulfase | Naglazyme ™ |
| Nesiritide | Natrecor ® |
| Pegfilgrastim | Neulasta ™ |
| Oprelvekin | Neumega ® |
| Filgrastim | Neupogen ® |
| Fanolesomab | NeutroSpec ™ (formerly LeuTech ®) |
| somatropin [rDNA] | Norditropin ®/Norditropin Nordiflex ® |
| Mitoxantrone | Novantrone ® |
| insulin; zinc suspension; | Novolin L ® |
| insulin; isophane suspension | Novolin N ® |
| insulin, regular, | Novolin R ® |
| Insulin | Novolin ® |
| coagulation factor VIIa | NovoSeven ® |
| Somatropin | Nutropin ® |
| immunoglobulin intravenous | Octagam ® |

TABLE I-continued

| Protein Product | Reference Listed Drug |
|---|---|
| PEG-L-asparaginase | Oncaspar ® |
| abatacept, fully human soluable fusion protein | Orencia ™ |
| muromomab-CD3 | Orthoclone OKT3 ® |
| high-molecular weight hyaluronan | Orthovisc ® |
| human chorionic gonadotropin | Ovidrel ® |
| live attenuated *Bacillus* Calmette-Guerin | Pacis ® |
| peginterferon alfa-2a | Pegasys ® |
| pegylated version of interferon alfa-2b | PEG-Intron ™ |
| Abarelix (injectable suspension); gonadotropin-releasing hormone antagonist | Plenaxis ™ |
| epoietin alfa | Procrit ® |
| Aldesleukin | Proleukin, IL-2 ® |
| Somatrem | Protropin ® |
| dornase alfa | Pulmozyme ® |
| Efalizumab; selective, reversible T-cell blocker | RAPTIVA ™ |
| combination of ribavirin and alpha interferon | Rebetron ™ |
| Interferon beta 1a | Rebif ® |
| antihemophilic factor | Recombinate ® rAHF/ |
| antihemophilic factor | ReFacto ® |
| Lepirudin | Refludan ® |
| Infliximab | REMICADE ® |
| Abciximab | ReoPro ™ |
| Reteplase | Retavase ™ |
| Rituxima | Rituxan ™ |
| interferon alfa-2$^a$ | Roferon-A ® |
| Somatropin | Saizen ® |
| synthetic porcine secretin | SecreFlo ™ |
| Basiliximab | Simulect ® |
| Eculizumab | SOLIRIS (R) |
| Pegvisomant | SOMAVERT ® |
| Palivizumab; recombinantly produced, humanized mAb | Synagis ™ |
| thyrotropin alfa | Thyrogen ® |
| Tenecteplase | TNKase ™ |
| Natalizumab | TYSABRI ® |
| human immune globulin intravenous 5% and 10% solutions | Venoglobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| Daclizumab | Zenapax ® |
| ibritumomab tiuxetan | Zevalin ™ |
| Somatotropin | Zorbtive ™ (Serostim ®) |

In embodiments, the polypeptide is a hormone, blood clotting/coagulation factor, cytokine/growth factor, antibody molecule, fusion protein, protein vaccine, or peptide as shown in Table 2.

TABLE 2

Exemplary Products

| Therapeutic Product type | Product | Trade Name |
|---|---|---|
| Hormone | Erythropoietin, Epoein-α | Epogen, Procrit |
|  | Darbepoetin-α | Aranesp |
|  | Growth hormone (GH), somatotropin | Genotropin, Humatrope, Norditropin, NovIVitropin, Nutropin, Omnitrope, Protropin, Siazen, Serostim, Valtropin |
|  | Human follicle-stimulating hormone (FSH) | Gonal-F, Follistim |
|  | Human chorionic gonadotropin | Ovidrel |
|  | Lutropin-α | Luveris |
|  | Glucagon | GlcaGen |
|  | Growth hormone releasing hormone (GHRH) | Geref |
|  | Secretin | ChiRhoStim (human peptide), SecreFlo (porcine peptide) |
|  | Thyroid stimulating hormone (TSH), thyrotropin | Thyrogen |
| Blood Clotting/Coagulation Factors | Factor VIIa | NovoSeven |
|  | Factor VIII | Bioclate, Helixate, Kogenate, Recombinate, ReFacto |
|  | Factor IX |  |

TABLE 2-continued

Exemplary Products

| Therapeutic Product type | Product | Trade Name |
|---|---|---|
| | Antithrombin III (AT-III) | Benefix |
| | Protein C concentrate | Thrombate III |
| | | Ceprotin |
| Cytokine/Growth factor | Type I alpha-interferon | Infergen |
| | Interferon-αn3 (IFNαn3) | Alferon N |
| | Interferon-β1a (rIFN- β) | Avonex, Rebif |
| | Interferon-β1b (rIFN- β) | Betaseron |
| | Interferon-γ1b (IFN γ) | Actimmune |
| | Aldesleukin (interleukin 2(IL2), epidermal theymocyte activating factor; | Proleukin |
| | ETAF Palifermin (keratinocyte growth factor; KGF) | Kepivance |
| | Becaplemin (platelet-derived growth factor; PDGF) | Regranex |
| | Anakinra (recombinant IL1 antagonist) | Anril, Kineret |
| Antibody molecules | Bevacizumab (VEGFA mAb) | Avastin |
| | Cetuximab (EGFR mAb) | Erbitux |
| | Panitumumab (EGFR mAb) | Vectibix |
| | Alemtuzumab (CD52 mAb) | Campath |
| | Rituximab (CD20 chimeric Ab) | Rituxan |
| | Trastuzumab (HER2/Neu mAb) | Herceptin |
| | Abatacept (CTLA Ab/Fc fusion) | Orencia |
| | Adalimumab (TNFαmAb) | Humira |
| | Etanercept (TNF receptor/Fc fusion) | Enbrel |
| | Infliximab (TNFαchimeric mAb) | Remicade |
| | Alefacept (CD2 fusion protein) | Amevive |
| | Efalizumab (CD11a mAb) | Raptiva |
| | Natalizumab (integrin α4 subunit mAb) | Tysabri |
| | Eculizumab (C5mAb) | Soliris |
| | Muromonab-CD3 | Orthoclone, OKT3 |
| Other: Fusion proteins/Protein vaccines/Peptides | Insulin | Humulin, Novolin |
| | Hepatitis B surface antigen (HBsAg) | Engerix, Recombivax HB |
| | HPV vaccine | Gardasil |
| | OspA | LYMErix |
| | Anti-Rhesus(Rh) immunoglobulin G | Rhophylac |
| | Enfuvirtide | Fuzeon |
| | Spider silk, e.g., fibrion | QMONOS |

In embodiments, the protein is multispecific protein, e.g., a bispecific antibody as shown in Table 3.

TABLE 3

Bispecific Formats

| Name (other names, sponsoring organizations) | BsAb format | Targets | Proposed mechanisms of action | Development stages | Diseases (or healthy volunteers) |
|---|---|---|---|---|---|
| Catumaxomab (Removab ®, Fresenius Biotech, Trion Pharma, Neopharm) | BsIgG: Triomab | CD3, EpCAM | Retargeting of T cells to tumor, Fc mediated effector functions | Approved in EU | Malignant ascites in EpCAM positive tumors |
| Ertumaxomab (Neovii Biotech, Fresenius Biotech) | BsIgG: Triomab | CD3, HER2 | Retargeting of T cells to tumor | Phase I/II | Advanced solid tumors |

TABLE 3-continued

Bispecific Formats

| Name (other names, sponsoring organizations) | BsAb format | Targets | Proposed mechanisms of action | Development stages | Diseases (or healthy volunteers) |
|---|---|---|---|---|---|
| Blinatumomab (Blincyto ®, AMG 103, MT 103, MEDI 538, Amgen) | BiTE | CD3, CD19 | Retargeting of T cells to tumor | Approved in USA Phase II and III Phase II Phase I | Precursor B-cell ALL ALL DLBCL NHL |
| REGN1979 (Regeneron) | BsAb | CD3, CD20 | | | |
| Solitomab (AMG 110, MT110, Amgen) | BiTE | CD3, EpCAM | Retargeting of T cells to tumor | Phase I | Solid tumors |
| MEDI 565 (AMG 211, MedImmune, Amgen) | BiTE | CD3, CEA | Retargeting of T cells to tumor | Phase I | Gastrointestinal adenocancinoma |
| RO6958688 (Roche) | BsAb | CD3, CEA | | | |
| BAY2010112 (AMG 212, Bayer; Amgen) | BiTE | CD3, PSMA | Retargeting of T cells to tumor | Phase I | Prostate cancer |
| MGD006 (Macrogenics) | DART | CD3, CD123 | Retargeting of T cells to tumor | Phase I | AML |
| MGD007 (Macrogenics) | DART | CD3, gpA33 | Retargeting of T cells to tumor | Phase I | Colorectal cancer |
| MGD011 (Macrogenics) | DART | CD19, CD3 | | | |
| SCORPION (Emergent Biosolutions, Trubion) | BsAb | CD3, CD19 | Retargeting of T cells to tumor | | |
| AFM11 (Affimed Therapeutics) | TandAb | CD3, CD19 | Retargeting of T cells to tumor | Phase I | NHL and ALL |
| AFM12 (Affimed Therapeutics) | TandAb | CD19, CD16 | Retargeting of NK cells to tumor cells | | |
| AFM13 (Affimed Therapeutics) | TandAb | CD30, CD16A | Retargeting of NK cells to tumor cells | Phase II | Hodgkin's Lymphoma |
| GD2 (Barbara Ann Karmanos Cancer Institute) | T cells preloaded with BsAb | CD3, GD2 | Retargeting of T cells to tumor | Phase I/II | Neuroblastoma and osteosarcoma |
| pGD2 (Barbara Ann Karmanos Cancer Institute) | T cells preloaded with BsAb | CD3, Her2 | Retargeting of T cells to tumor | Phase II | Metastatic breast cancer |
| EGFRBi-armed autologous activated T cells (Roger Williams Medical Center) | T cells preloaded with BsAb | CD3, EGFR | Autologous activated T cells to EGFR-positive tumor | Phase I | Lung and other solid tumors |
| Anti-EGFR-armed activated T-cells (Barbara Ann Karmanos Cancer Institute) | T cells preloaded with BsAb | CD3, EGFR | Autologous activated T cells to EGFR-positive tumor | Phase I | Colon and pancreatic cancers |
| rM28 (University Hospital Tübingen) | Tandem scFv | CD28, MAPG | Retargeting of T cells to tumor | Phase II | Metastatic melanoma |
| IMCgp100 (Immunocore) | ImmTAC | CD3, peptide MHC | Retargeting of T cells to tumor | Phase I/II | Metastatic melanoma |
| DT2219ARL (NCI, University of Minnesota) | 2 scFv linked to diphtheria toxin | CD19, CD22 | Targeting of protein toxin to tumor | Phase I | B cell leukemia or lymphoma |
| XmAb5871 (Xencor) | BsAb | CD19, CD32b | | | |
| NI-1701 (NovImmune) | BsAb | CD47, CD19 | | | |
| MM-111 (Merrimack) | BsAb | ErbB2, ErbB3 | | | |
| MM-141 (Merrimack) | BsAb | IGF-1R, ErbB3 | | | |
| NA (Merus) | BsAb | HER2, HER3 | | | |
| NA (Merus) | BsAb | CD3, CLEC12A | | | |
| NA (Merus) | BsAb | EGFR, HER3 | | | |
| NA (Merus) | BsAb | PD1, undisclosed | | | |
| NA (Merus) | BsAb | CD3, undisclosed | | | |
| Duligotuzumab (MEHD7945A, Genentech, Roche) | DAF | EGFR, HER3 | Blockade of 2 receptors, ADCC | Phase I and II Phase II | Head and neck cancer Colorectal cancer |
| LY3164530 (Eli Lily) | Not disclosed | EGFR, MET | Blockade of 2 receptors | Phase I | Advanced or metastatic cancer |

TABLE 3-continued

Bispecific Formats

| Name (other names, sponsoring organizations) | BsAb format | Targets | Proposed mechanisms of action | Development stages | Diseases (or healthy volunteers) |
|---|---|---|---|---|---|
| MM-111 (Merrimack Pharmaceuticals) | HSA body | HER2, HER3 | Blockade of 2 receptors | Phase II Phase I | Gastric and esophageal cancers Breast cancer |
| MM-141, (Merrimack Pharmaceuticals) | IgG-scFv | IGF-1R, HER3 | Blockade of 2 receptors | Phase I | Advanced solid tumors |
| RG7221 (RO5520985, Roche) | CrossMab | Ang2, VEGF A | Blockade of 2 proangiogenics | Phase I | Solid tumors |
| RG7716 (Roche) | CrossMab | Ang2, VEGF A | Blockade of 2 proangiogenics | Phase I | Wet AMD |
| OMP-305B83 (OncoMed) | BsAb | DLL4/VEGF | | | |
| TF2 (Immunomedics) | Dock and lock | CEA, HSG | Pretargeting tumor for PET or radioimaging | Phase II | Colorectal, breast and lung cancers |
| ABT-981 (AbbVie) | DVD-Ig | IL-1α, IL-1β | Blockade of 2 proinflammatory cytokines | Phase II | Osteoarthritis |
| ABT-122 (AbbVie) | DVD-Ig | TNF, IL-17A | Blockade of 2 proinflammatory cytokines | Phase II | Rheumatoid arthritis |
| COVA322 | IgG-fynomer | TNF, IL17A | Blockade of 2 proinflammatory cytokines | Phase I/II | Plaque psoriasis |
| SAR156597 (Sanofi) | Tetravalent bispecific tandem IgG | IL-13, IL-4 | Blockade of 2 proinflammatory cytokines | Phase I | Idiopathic pulmonary fibrosis |
| GSK2434735 (GSK) | Dual-targeting domain | IL-13, IL-4 | Blockade of 2 proinflammatory cytokines | Phase I | (Healthy volunteers) |
| Ozoralizumab (ATN103, Ablynx) | Nanobody | TNF, HSA | Blockade of proinflammatory cytokine, binds to HSA to increase half-life | Phase II | Rheumatoid arthritis |
| ALX-0761 (Merck Serono, Ablynx) | Nanobody | IL-17A/F, HSA | Blockade of 2 proinflammatory cytokines, binds to HSA to increase half-life | Phase I | (Healthy volunteers) |
| ALX-0061 (AbbVie, Ablynx; | Nanobody | IL-6R, HSA | Blockade of proinflammatory cytokine, binds to HSA to increase half-life | Phase I/II | Rheumatoid arthritis |
| ALX-0141 (Ablynx, Eddingpharm) | Nanobody | RANKL, HSA | Blockade of bone resorption, binds to HSA to increase half-life | Phase I | Postmenopausal bone loss |
| RG6013/ACE910 (Chugai, Roche) | ART-Ig | Factor IXa, factor X | Plasma coagulation | Phase II | Hemophilia |

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged in whole or in part. Furthermore, those of ordinary skill in the art will appreciate that the foregoing description is by way of example only, and is not intended to limit the invention so further described in such appended claims.

What is claimed:

1. A bioprocess system comprising:
a cell culture apparatus for growing and harvesting cell cultures, the cell culture apparatus comprising a plurality of cell culture chambers in a stacked arrangement, the cell culture apparatus including at least one bioprocess tube having a diameter and a wall thickness, the at least one bioprocess tube being comprised of a thermoplastic elastomer;
a plurality of bioprocess containers, the containers defining a hollow enclosure for holding a cell culture media, each container including a cell culture linking tube in communication with the hollow enclosure, the linking tube having a diameter, a wall thickness and being comprised of a material that are compatible with the diameter, wall thickness and thermoplastic elastomer of the bioprocess tube;
wherein the cell culture linking tube of each bioprocess container is configured to be welded to the bioprocess tube of the cell culture apparatus so that each bioprocess container can be selectively placed in fluid communication with the cell culture apparatus, wherein each cell culture linking tube and the bioprocess tube have a wall thickness of at least 2.25 mm, and have an inside diameter of from 7.5 mm to 12.5 mm; and wherein one of the cell culture linking tubes is connected to the bioprocess tube of the cell culture apparatus, the cell culture linking tube having been welded to the bioprocess tube to form a weld structure, the weld structure including a leak proof flange encircling the location where the cell culture linking tube has been attached to the bioprocess tube and being formed from the cell culture linking tube and the bioprocess tube during welding; and wherein the leak proof flange has a height of greater than 0.2 mm.

2. A bioprocess system as defined in claim 1, further comprising a biowelding apparatus configured to simultaneously cut and weld together the bioprocess tube with one of the cell culture linking tubes for placing the cell culture apparatus in fluid communication with one of the bioprocess containers for feeding materials or removing materials from the cell culture apparatus without creating an open connection in the bioprocess tube.

3. A bioprocess system as defined in claim 2, further comprising at least one flow stopper association with the bioprocess tube.

4. A bioprocess system as defined in claim 1, wherein the thermoplastic elastomer comprises a silicone polymer, a polyvinyl chloride polymer, a polypropylene polymer, a polyethylene polymer, or a polyester polymer.

5. A bioprocess system as defined in claim 1, wherein the bioprocess tube has a wall thickness of from 2.75 mm to 3.75 mm.

6. A bioprocess system as defined in claim 1, wherein the bioprocess tube and the linking tubes have the same diameter, wall thickness and are made from the same thermoplastic elastomer.

7. A bioprocess system as defined in claim 1, wherein the system includes at least three bioprocess containers, wherein at least one of the containers contains a reagent and at least one of the containers is empty for receiving a liquid media from the cell culture apparatus.

8. A bioprocess system as defined in claim 1, wherein the hollow enclosure of the bioprocess containers has a volume of from 0.5 liters to 25 liters.

9. A method for delivering materials to a cell culture apparatus comprising;

blocking flow of fluids through an end portion of the at least one bioprocess tube, the bioprocess tube being connected to and in fluid communication with a cell culture apparatus, the cell culture apparatus including a plurality of cell culture chambers in a stacked arrangement, the bioprocess tube comprising a thermoplastic elastomer having an inside diameter and a wall thickness, the bioprocess tube being configured to deliver and remove materials from the cell culture apparatus;

blocking flow of fluids through an end portion of a cell culture linking tube in communication with a bioprocess container, the bioprocess container containing a cell culture media;

cutting and welding together the end portions of the bioprocess tube and a cell culture linking tube, the bioprocess tube and the cell culture linking tube having wall thicknesses of at least 2.25 mm and having an inside diameter of from 7.5 mm to 12.5 mm;

unblocking fluid flow through the bioprocess tube and the cell culture linking tube; and feeding the cell culture media from the bioprocess container through the linking tube and bioprocess tube to the cell culture apparatus, wherein the end portion of the bioprocess tube and the end portion of the cell culture linking tube form a weld structure, the weld structure including a link proof flange encircling the location where the bioprocess tube has been welded to the cell culture linking tube, the flange having a height of greater than 0.2 mm.

10. A method as defined in claim 9, further comprising the steps of blocking fluid flow through the end portion of the at least one bioprocess tube;

blocking fluid flow through the end portion of the cell culture linking tube;

blocking fluid flow through the bioprocess tube;

blocking fluid flow through an end portion of a second cell culture linking tube in communication with a second bioprocess container, the second bioprocess container containing a cell culture media;

cutting and welding together the bioprocess tube with the end portion of the second cell culture linking tube, the bioprocess tube and the end portion of the second cell culture linking tube being cut and welded together in a manner so that an open connection of the bioprocess tube is never formed during the cutting and welding procedure;

unblocking fluid flow through the bioprocess tube and the second cell culture linking tube; and feeding the cell culture media from the second bioprocess container through the second cell culture linking tube and bioprocess tube into the cell culture apparatus.

11. A method as defined in claim 9, wherein the cutting and welding together of the end portions of the bioprocess tube and the cell culture linking tube do not occur within a ventilated enclosure.

12. A method as defined in claim 9, wherein the cell culture media comprises viable cells for inoculating the cell culture apparatus and for growing a cell culture within the cell culture apparatus.

13. A method as defined in claim 9, wherein the end portion of the bioprocess tube is cut and welded to the end portion of the cell culture linking tube without creating an open connection.

14. A method as defined in claim 10, wherein the cell culture media comprises viable cells for inoculating the cell culture apparatus and for growing a cell culture within the cell culture apparatus, and wherein the cell culture media contained in the second bioprocess container comprises a cell nutrient composition.

15. A method as defined in claim 10, wherein the cell culture media contained in the second bioprocess container comprises a proteolytic enzyme for detaching and harvesting a cell culture from the cell culture apparatus.

16. A method as defined in claim 10, wherein the second cell culture linking tube includes a Y connection leading to a first Y tube and a second Y tube, the first Y tube being connected to the second bioprocess container, the second Y tube being connected to a third bioprocess container, the cell culture media contained in the second bioprocess container comprising a proteolytic enzyme for detaching and harvesting a cell culture from the cell culture apparatus, the third bioprocess container containing a quench composition, and wherein the quench composition is fed into the cell culture apparatus after the proteolytic enzyme.

17. A method as defined in claim 16, wherein the cell culture apparatus is emptied into the second bioprocess container or into the third bioprocess container after the proteolytic enzyme and the quench composition have been fed into the cell culture apparatus in order to harvest a cell culture from the cell culture apparatus.

\* \* \* \* \*